(12) United States Patent
Xu et al.

(10) Patent No.: US 11,505,542 B2
(45) Date of Patent: Nov. 22, 2022

(54) PREPARATION METHOD FOR MORPHOLINQUINAZOLINE COMPOUND AND INTERMEDIATES THEREOF

(71) Applicant: SHANGHAI YINGLI PHARMACEUTICAL CO., LTD, Shanghai (CN)

(72) Inventors: Zusheng Xu, Shanghai (CN); Jizhi Li, Shanghai (CN); Jianfeng Wu, Shanghai (CN); Yangtong Lou, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 17/423,153

(22) PCT Filed: Dec. 24, 2019

(86) PCT No.: PCT/CN2019/127763
§ 371 (c)(1),
(2) Date: Jul. 15, 2021

(87) PCT Pub. No.: WO2020/147525
PCT Pub. Date: Jul. 23, 2020

(65) Prior Publication Data
US 2022/0127248 A1    Apr. 28, 2022

(30) Foreign Application Priority Data

Jan. 16, 2019    (CN) .......................... 201910040918.1

(51) Int. Cl.
*C07D 401/04* (2006.01)
*C07D 401/14* (2006.01)
(Continued)

(52) U.S. Cl.
CPC ......... *C07D 401/14* (2013.01); *C07D 239/78* (2013.01); *C07D 401/04* (2013.01)

(58) Field of Classification Search
CPC .. C07D 401/14; C07D 239/78; C07D 401/04; C07D 239/95; A61K 31/5377
See application file for complete search history.

(56) References Cited

U.S. PATENT DOCUMENTS
2016/0244432 A1    8/2016   Xu et al.

FOREIGN PATENT DOCUMENTS
CN    106831721 A    6/2017
WO    WO-2010059627 A1    5/2010
(Continued)

OTHER PUBLICATIONS

Pospisilova Monika et al. "Novel quinazolin-4-one derivatives as potentiating agents of doxorubicin cytotoxicity", *Bioorganic Chemistry*, vol. 82, Oct. 6, 2018 (Oct. 6, 2018), pp. 204-210.
(Continued)

*Primary Examiner* — John M Mauro
(74) *Attorney, Agent, or Firm* — Harness, Dickey & Pierce, P.L.C.

(57) ABSTRACT

The present disclosure relates to a preparation method morpholinquinazoline compound and a midbody thereof. The preparation method for morpholinquinazoline compound comprises the following steps: S1, performing a Suzuki reaction of compound S and compound IV as represented by the following formula, so as to obtain compound V; step S2, performing a reaction of methylsufonyl chloride and compound V in an organic solvent as represented by the following formula, so as to obtain compound VI; and S3, performing a coupled reaction of compound VII and compound VI in a solvent as represented by the following formula, so as to obtain compound YY-20394. The preparation method has the advantages of higher yield, better selectivity, simple operation and mild reaction condition, and is applicable to industrial production.

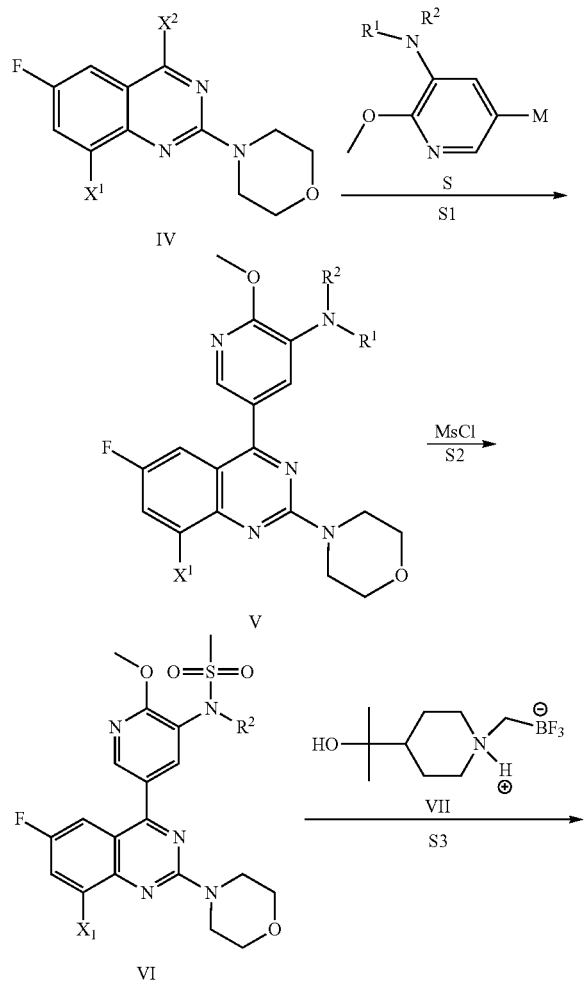

(Continued)

-continued

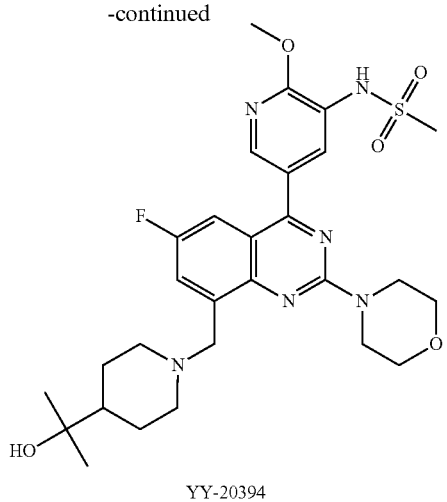

YY-20394

20 Claims, No Drawings

(51) Int. Cl.
*C07D 239/78* (2006.01)
*C07D 239/95* (2006.01)
*A61K 31/5377* (2006.01)

(56) References Cited

FOREIGN PATENT DOCUMENTS

| WO | WO-2015055071 A1 | 4/2015 |
| WO | WO-2016164675 A1 | 10/2016 |

OTHER PUBLICATIONS

Heppell Jacob T. et al. "Functionalization of Quinazolin-4-ones Part 3: Synthesis, Structures Elucidation, DNA-PK, PI3K, and Cytotoxicity of Novel 8-Aryl-2-morpholino-quinazolin-4-ones", *Journal of Heterocyclic Chemistry*, vol. 56, Nov. 28, 2018 (Nov. 28, 2018), pp. 124-141.

Vanhaesebroeck Bart et al. "Phosphoinositide 3-kinases: a conserved family of signal transducers", Trends. Biochem. Sci., 1997, 22, 267-272.

Vivanco Igor et al. "The Phosphatidylinositol 3-Kinase-AKT Pathway in Human Cancer", Nat. Rev. Cancer 2002, 2, 489-501.

International Search Report (in Chinese and English) dated Mar. 23, 2020 issued in PCT application PCT/CN2019/127763.

Written Opinion (in Chinese and English) of International Search Authority dated Mar. 23, 2020 issued in PCT application PCT/CN2019/127763.

First Office Action dated Nov. 19, 2021 issued in Korean Patent Application No. 10-2021-7025800.

PREPARATION METHOD FOR MORPHOLINQUINAZOLINE COMPOUND AND INTERMEDIATES THEREOF

The present application claims priority to Chinese Patent Application No. 2019100409181 filed on Jan. 16, 2019. The contents of which are incorporated herein by reference in their entireties.

TECHNICAL FIELD

The present invention relates to a method for preparing a morpholinyl quinazoline compound and an intermediate of the same.

BACKGROUND

The morpholinyl quinazoline compound of formula YY-20394, with a chemical structure of

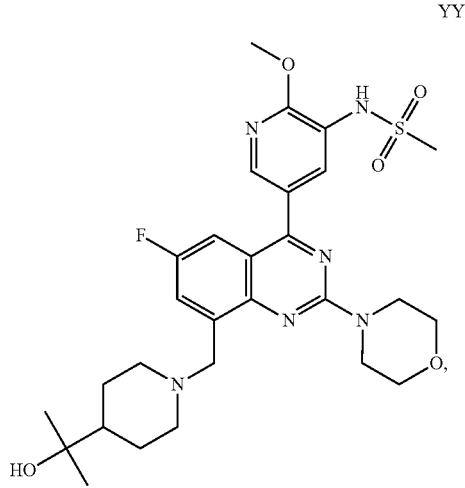

YY-20394 has activity for inhibiting phosphatidylinositol 3-kinase δ (PI3K-δ).

PI3K-δ is an intracellular phosphatidylinositol kinase, which catalyzes the phosphorylation of 3-hydroxyl in phosphatidylinositol. PI3Ks can be classified into classes I, II and III. Among these, class I PI3Ks that can be activated by cell surface receptors are most widely studied. Class I PI3Ks in mammalian cells are further classified by structure and receptor into classes Ia and Ib, which transmit signals from tyrosine kinase-linked receptors and G protein-coupled receptors, respectively. Class Ia PI3Ks include PI3K-α, PI3K-β and PI3K-δ subtypes, and class Ib PI3Ks include the PI3K-γ subtype (Trends. Biochem. Sci., 1997, 22, 267-272). Class Ia PI3Ks are dimeric proteins consisting of a catalytic subunit p110 and a regulatory subunit p85, with dual activities of lipoid kinases and protein kinases (Nat. Rev. Cancer, 2002, 2, 489-501), and are considered relevant to cell proliferation, tumorigenesis, immune diseases and inflammation-associated diseases.

Patent No. WO2015055071A1 discloses compound YY-20394 and a method for preparing the same. In that patent, with starting material 2-amino-5-fluorobenzoic acid, a trichloride intermediate I-11 is synthesized through 3 reactions, and the product YY-20394 is then obtained through four reactions. However, the step for generating compound I-11-a from compound I-11 has poor selectivity, produces more impurities, and has yield of only 28% for compound I-11-a. Thus the path is mainly suitable for the chemically structural modification of a drug, rather than industrial manufacture.

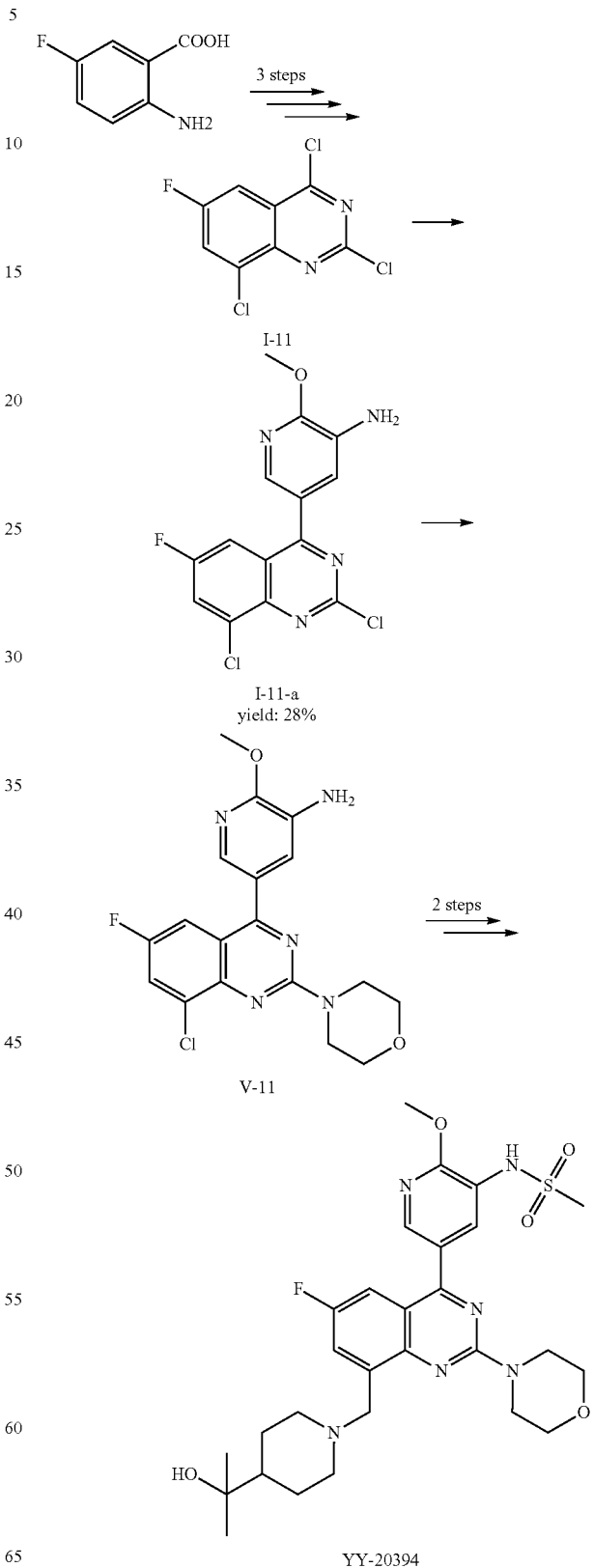

In view of this, it is an urgent need to develop a method for preparing compound YY-20394, which features high yield, good selectivity to avoid a byproduct at position 2 on the quinazoline ring, ease-to-operate and mild reaction conditions, and is suitable for industrial manufacture.

SUMMARY

The present invention provides a method for preparing a morpholinyl quinazoline compound and an intermediate of the same, which is different from the prior art. The method features high yield, good selectivity to avoid a byproduct at position 2 on the quinazoline ring and increase the selectivity of the Suzuki reaction at position 4 of the quinazoline ring, ease-to-operate and mild reaction conditions, and is suitable for industrial manufacture.

The present invention is implemented by the following technical scheme.

The present invention provides a method for preparing a compound of formula V, comprising:

in the action of a palladium catalyst and an alkaline reagent, performing a Suzuki reaction of compound S and compound IV as represented by the following formula in a solvent to obtain compound V;

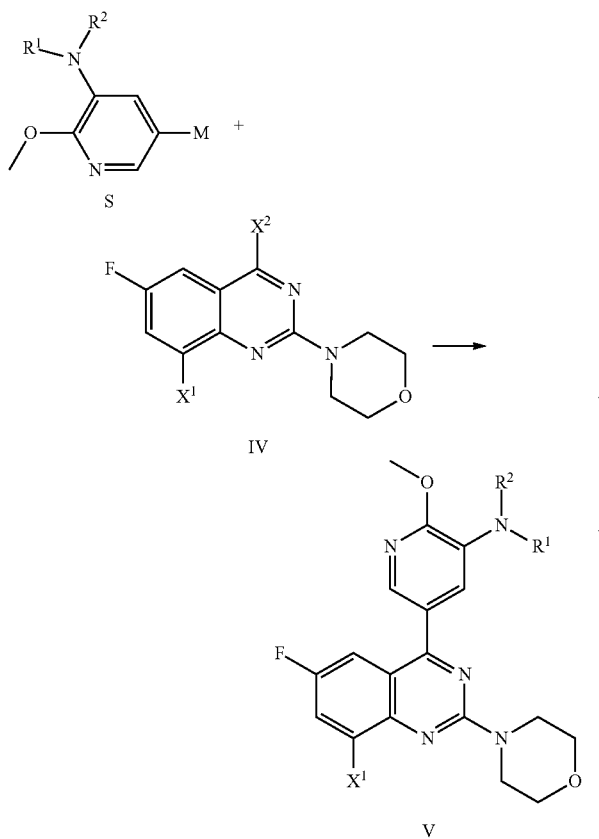

wherein $R^1$ and $R^2$ are independently H or

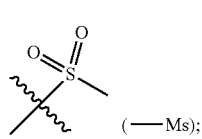

(—Ms);

M is

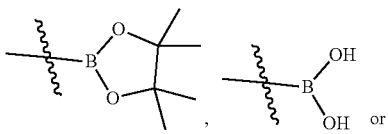

—$BF_3K$;
$X^1$ is Cl or Br;
$X^2$ is halogen,

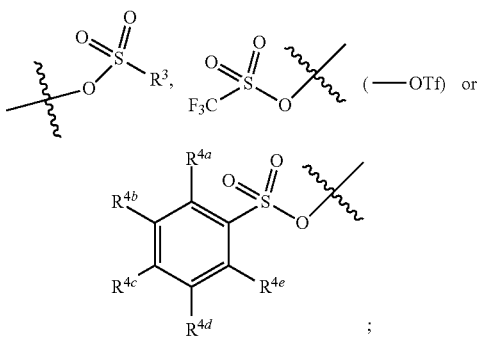

$R^3$ is $C_{1-4}$ alkyl;
$R^{4a}$, $R^{4b}$, $R^{4c}$, $R^{4d}$ and $R^{4e}$ are independently H, $C_{1-6}$ alkyl, nitro or halogen.

In $R^3$, the $C_{1-4}$ alkyl is preferably methyl, ethyl, n-propyl, isopropyl, n-butyl,

or tert-butyl, more preferably methyl.

In $X^2$, the halogen is preferably Cl, Br or I, more preferably Cl.

In $R^{4a}$, $R^{4b}$, $R^{4c}$, $R^{4d}$ and $R^{4e}$, the halogen is independently and preferably Cl, Br or I.

In $R^{4a}$, $R^{4b}$, $R^{4c}$, $R^{4d}$ and $R^{4e}$, the $C_{1-6}$ alkyl is independently and preferably $C_{1-3}$ alkyl, more preferably methyl, ethyl, n-propyl or isopropyl, still more preferably methyl.

In one embodiment, M is

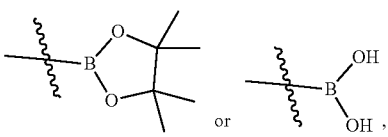

preferably

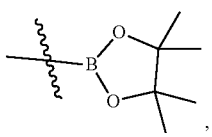 [SMILES: *B1OC(C)(C)C(C)(C)O1]

In one embodiment, $X^1$ is Cl.

In one embodiment, $X^2$ is halogen,

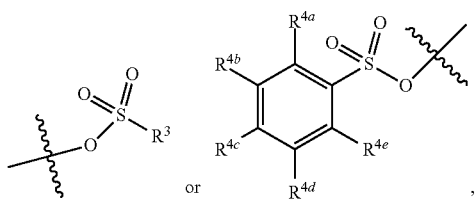

or preferably

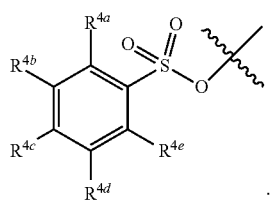

In one embodiment, $R^{4a}$, $R^{4b}$, $R^{4d}$ and $R^{4e}$ are independently H.

In one embodiment, $R^{4c}$ is preferably nitro or $C_{1-6}$ alkyl, more preferably $C_{1-6}$ alkyl.

In one embodiment, when $X^2$ is

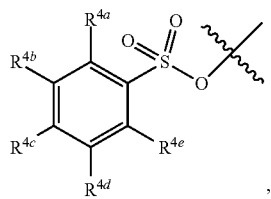

then the

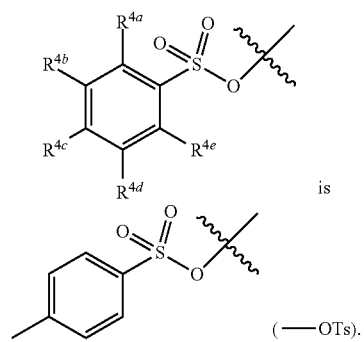

(—OTs).

The Suzuki reaction may be a conventional reaction in the art for such reactions.

In the Suzuki reaction, the palladium catalyst may be a conventional palladium catalyst in the art for such reactions, preferably one or more of tetrakis(triphenylphosphine)palladium (Pd(PPh$_3$)$_4$), palladium acetate Pd(OAc)$_2$, bis(triphenylphosphine)palladium dichloride (PdCl$_2$(PPh$_3$)$_2$), dichlorobis(tri-o-tolylphosphine)palladium(II) (PdCl$_2$[P(o-tol)$_3$]$_2$), tris(dibenzylideneacetone) dipalladium (Pd$_2$(dba)$_3$), bis(tri-tert-butylphosphine)palladium (Pd[P(t-Bu)$_3$]$_2$), [1,1-bis(diphenylphosphino)ferrocene]palladium dichloride (PdCl$_2$(dppf)) and [1,1'-bis(diphenylphosphino) ferrocene] palladium(II)dichloride dichloromethane complex (PdCl$_2$(dppf)DCM), more preferably tetrakis(triphenylphosphine) palladium.

In the Suzuki reaction, the palladium catalyst may also react in the presence of a ligand. The ligand may be a conventional ligand in the art for such reactions, preferably one or more of triphenylphosphine (PPh$_3$), tris(o-tolyl) phosphine (P(o-tol)$_3$), tri-tert-butylphosphine tetrafluoroborate, 2-dicyclohexylphosphino-2',4',6'-triisopropylbiphenyl (x-Phos), 2-dicyclohexylphosphino-2',6'-dimethoxy-biphenyl (s-Phos) and 2-dicyclohexylphosphino-2',6'-diisopropoxy-1,1'-biphenyl (Ru-Phos).

In the Suzuki reaction, the molar ratio of the palladium catalyst to compound IV may be 0.01-0.5, preferably 0.02-0.2, for example, 0.06.

In the Suzuki reaction, the solvent may be a conventional solvent in the art for such reactions, preferably a mixed solvent of an organic solvent and water. The organic solvent may be a conventional organic solvent in the art for such reactions, preferably one or more of aromatic hydrocarbon solvent, alcohol solvent, chlorinated hydrocarbon solvent and ether solvent, more preferably a mixed solvent of aromatic hydrocarbon solvent and alcohol solvent. The aromatic hydrocarbon solvent and the alcohol solvent are preferably toluene and isopropanol. The volume ratio of the aromatic hydrocarbon solvent to the alcohol solvent is preferably 1:1-5:1, more preferably 3:1-5:1, for example, 4:1. The volume ratio of the organic solvent to water may be a conventional volume ratio in the art for such reactions, preferably 1:1-10:1, more preferably 5:1-10:1.

In the Suzuki reaction, the amount of the mixed solvent is not specified as long as the reaction is not affected.

In the Suzuki reaction, the alkaline reagent may be a conventional alkaline reagent in the art for such reactions, preferably one or more of alkali metal carbonate, alkali metal fluoride, alkali metal phosphate, alkali metal tert-butoxide and alkali metal hydroxide. The alkali metal carbonate may be one or more of sodium carbonate, potassium carbonate and cesium carbonate, preferably potassium carbonate. The alkali metal fluoride may be potassium fluoride. The alkali metal phosphate may be potassium phosphate. The alkali metal tert-butoxide may be sodium tert-butoxide and/or potassium tert-butoxide. The alkali metal hydroxide may be one or more of sodium hydroxide, potassium hydroxide and lithium hydroxide.

In the Suzuki reaction, the molar ratio of the alkaline reagent to compound IV may be 1-10, for example, 1.2, for another example, 1.7, preferably 2-10, for example, 9.

In the Suzuki reaction, the molar ratio of compound S to compound IV may be 0.9-3, preferably 0.9-1.5, for example, 1.0, for another example, 1.2.

In the Suzuki reaction, the temperature of the Suzuki reaction may be a conventional temperature in the art for such reactions, preferably 0-130° C., more preferably 20-70° C., for example, 45° C., for another example, 70° C.

The Suzuki reaction may be performed in a protective gas atmosphere. The protective gas may be a conventional protective gas in the art for such reactions, for example, nitrogen, for another example, argon.

The monitoring of the Suzuki reaction may be a conventional monitoring in the art for such reactions, for example, TLC, for another example, LC-MS. Generally, the complete disappearance of compound IV or no further reaction is considered as the end of the reaction. The time for the Suzuki reaction is preferably 1-18 h, for example, 12 h, for another example, 7 h, for still another example, 1 h.

In the Suzuki reaction, compound S is preferably

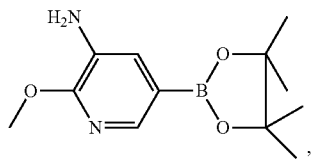
S-11

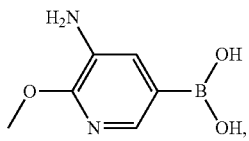
S-21

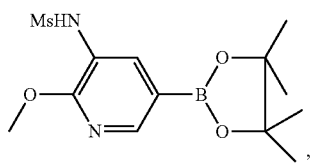
T-11

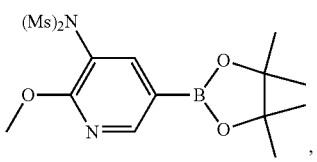
T-12

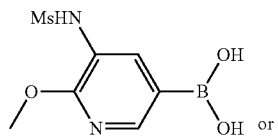
T-21

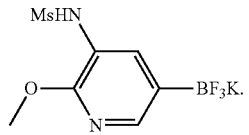
T-31

In the Suzuki reaction, compound IV is preferably

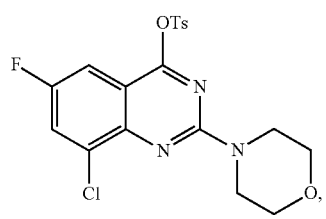
IV-11

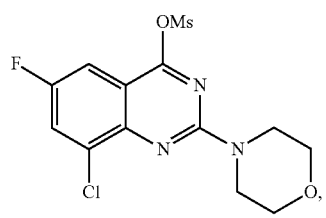
IV-12

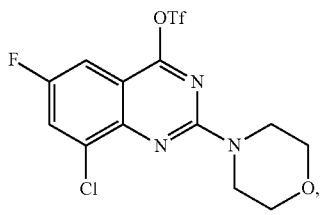
IV-13

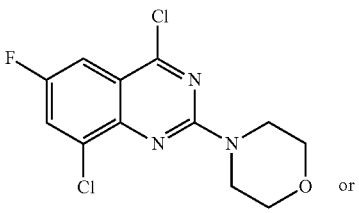
IV-14 or

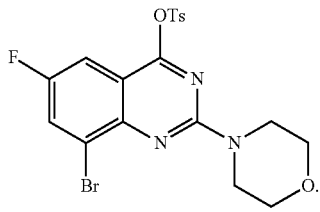
IV-21

After the Suzuki reaction is completed, the method may further comprise the following post-treatment steps: cooling the reaction solution after the reaction to room temperature, extracting, concentrating, and performing column chromatography.

The method for preparing the compound of formula V may further comprises a method for preparing compound IV, wherein the method is method 1 or method 2:

method 1 comprising: performing a halogenation reaction of compound III and "phosphorus oxyhalide and/or phosphorus halide" as represented by the following formula to obtain compound IV;

method 2 comprising: in the action of an alkaline reagent, performing a nucleophilic substitution reaction of compound III and a sulfonation reagent to the as represented by the following formula in an organic solvent to obtain compound IV;

the sulfonation reagent is

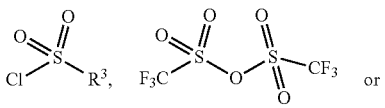
or

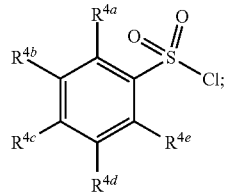

[Structure III: 6-fluoro-4-hydroxy-8-X¹-2-morpholinoquinazoline]

[Structure IV: 6-fluoro-4-X²-8-X¹-2-morpholinoquinazoline]

wherein $R^3$, $R^{4a}$, $R^{4b}$, $R^{4c}$, $R^{4d}$, $R^{4e}$, $X^1$ and $X^2$ are as defined above;

when $X^2$ is halogen, the method for preparing compound IV is method 1;

when $X^2$ is

[Structures: sulfonate groups with R³, CF₃, and substituted phenyl with R^{4a}–R^{4e}]

, the method for preparing compound IV is method 2.

In method 1, the halogenation reaction may be a conventional reaction in the art for such reactions.

In method 1, the halogenation reaction is preferably a neat reaction.

In method 1, the halogen in the "phosphorus oxyhalide and/or phosphorus halide" is preferably Cl, Br or I, more preferably Cl.

In method 1, the molar ratio of the "phosphorus oxyhalide and/or phosphorus halide" to compound III may be greater than or equal to 1, preferably 1-30, for example, 20, for another example, 10.

In method 1, the temperature of the halogenation reaction may be a conventional temperature in the art for such reactions, preferably 20-130° C., more preferably 60-110° C., for example, 105° C.

In method 1, the monitoring of the halogenation reaction may be a conventional monitoring in the art for such reactions, for example, TLC, for another example, LC-MS. Generally, the complete disappearance of compound III is considered as the end of the reaction. The time for the halogenation reaction is preferably 2-24 h, for example, 3 h.

In method 1, after the halogenation reaction is completed, the method may further comprise the following post-treatment steps: quenching the reaction, extracting, washing, and concentrating.

In method 1, in the post-treatment steps, the reaction solution may be concentrated before the quenching.

In method 1, in the post-treatment steps, the quenching may be performed in a conventional manner in the art for such reactions, preferably by adding water, more preferably by adding ice-water.

In method 1, in the post-treatment steps, the procedures and conditions for extracting may be those conventional in the art for such reactions. The organic solvent for extracting may be a chlorinated hydrocarbon solvent, preferably dichloromethane.

In method 1, in the post-treatment steps, the washing may be a conventional washing in the art for such reactions, preferably washing with saturated aqueous sodium chloride.

In method 1, in the post-treatment steps, the procedures and conditions for concentrating may be those conventional in the art for such reactions, for example, concentration under reduced pressure.

In method 2, the alkaline reagent may be a conventional alkaline reagent in the art for such reactions, preferably a weak organic alkali and/or a weak inorganic alkali salt, more preferably a weak organic alkali. The weak organic alkali may be a tertiary amine weak organic alkali and/or a pyridine weak organic alkali. The tertiary amine weak organic alkali is preferably triethylamine (TEA) and/or N,N-diisopropylethylamine (DIPEA). The weak inorganic alkali salt may be an alkali metal carbonate, preferably potassium carbonate.

In method 2, when the sulfonation reagent is

[Structure: substituted phenylsulfonyl chloride with R^{4a}–R^{4e}]

the

[Structure: substituted phenylsulfonyl chloride with R^{4a}–R^{4e}]

is preferably

[Structure: p-toluenesulfonyl chloride]

In method 2, when the sulfonation reagent is

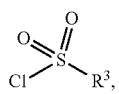

the

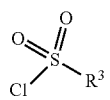

is preferably

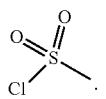

In method 2, the molar ratio of the sulfonation reagent to compound III may be a conventional molar ratio in the art for such reactions, preferably 1-1.5, for example, 1.

In method 2, the organic solvent may be a conventional organic solvent in the art for such reactions, preferably one or more of a nitrile solvent, a chlorinated hydrocarbon solvent and an ether solvent. The nitrile solvent is preferably acetonitrile. The chlorinated hydrocarbon solvent is preferably dichloromethane and/or chloroform. The ether solvent is preferably one or more of tetrahydrofuran, 1,4-dioxane and ethylene glycol dimethyl ether.

In method 2, the amount of the organic solvent is not specified as long as the reaction is not affected. For example, the volume-to-mass ratio of the organic solvent to compound III may be 5-15 mL/g, for example, 10 mL/g.

In method 2, the monitoring of the reaction may be a conventional monitoring in the art for such reactions, for example, TLC, for another example, LC-MS. Generally, the complete disappearance of compound III is considered as the end of the reaction. The time for the reaction is preferably 0.5-5 h, for example, 2 h.

In method 2, the temperature of the nucleophilic substitution reaction may be a conventional temperature in the art for such reactions, and may be 0-130° C., or 50-100° C., for example, 70° C., for another example, 80° C.

In method 2, after the nucleophilic substitution reaction is completed, the method may further comprise the following post-treatment steps: cooling the reaction solution after the reaction to room temperature, adding water until a solid is precipitated, filtering, and drying.

Compound III is preferably

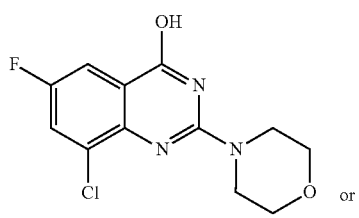

or

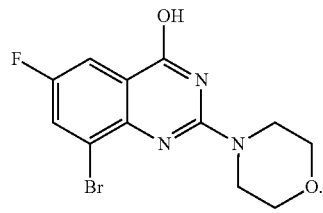

The method for preparing the compound of formula V may further comprise: performing a nucleophilic substitution reaction of compound II and compound A as represented by the following formula in an organic solvent to obtain compound III;

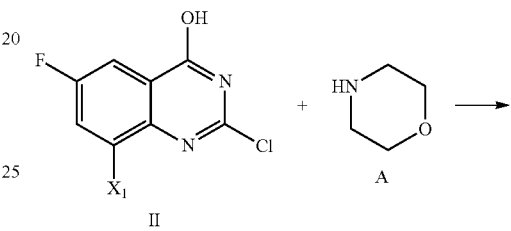

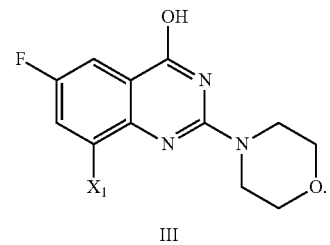

The conditions for the nucleophilic substitution reaction may be conventional conditions in the art for such reactions.

In the nucleophilic substitution reaction, the organic solvent may be a conventional organic solvent in the art for such reactions, preferably a polar aprotic solvent. The polar aprotic solvent may be an amide solvent. The amide solvent may be N,N-dimethylformamide (DMF) and/or N,N-dimethylacetamide (DMAC), preferably N,N-dimethylacetamide.

In the nucleophilic substitution reaction, the amount of the organic solvent is not specified as long as the reaction is not affected. For example, the volume-to-mass ratio of the organic solvent to compound II may be 5-15 mL/g, for example, 10 mL/g.

In the nucleophilic substitution reaction, the molar ratio of compound A to compound II may be a conventional molar ratio in the art for such reactions, and may be 1-10, or 1-3, for example, 2.4.

The temperature of the nucleophilic substitution reaction may be a conventional temperature in the art for such reactions, preferably 20-100° C., for example, 85° C.

The monitoring of the nucleophilic substitution reaction may be a conventional monitoring in the art for such reactions, for example, TLC, for another example, LC-MS. Generally, the complete disappearance of compound II is considered as the end of the reaction. The time for the nucleophilic substitution reaction is preferably 1-24 h, more preferably 1-5 h, for example, 2 h.

Compound II is preferably

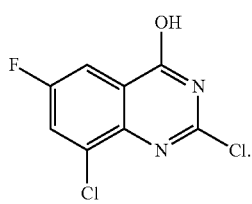

II-1

After the nucleophilic substitution reaction is completed, the method may further comprise the following post-treatment steps: cooling the reaction solution after the nucleophilic substitution reaction to room temperature, adding water until a solid is precipitated, filtering, and drying.

The method for preparing the compound of formula V may further comprise: in the action of an alkaline reagent, performing a reaction of compound I as represented by the following formula in a solvent to obtain compound II,

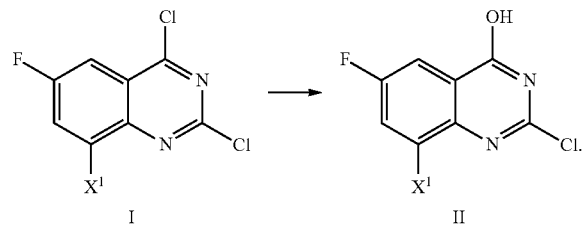

The reaction conditions may be conventional reaction conditions in the art for such reactions.

The solvent may be a conventional solvent in the art for such reactions, preferably a mixed solvent of an organic solvent and water. The organic solvent may be a conventional organic solvent in the art for such reactions, preferably one or more of a nitrile solvent, a ketone solvent, an ether solvent and an amide solvent, preferably a nitrile solvent. The nitrile solvent is preferably acetonitrile.

The amount of the solvent is not specified as long as the reaction is not affected.

The alkaline reagent may be a conventional alkaline reagent in the art for such reactions, preferably a strong inorganic alkali. The strong inorganic alkali may be one or more of sodium hydroxide, potassium hydroxide, lithium hydroxide and calcium hydroxide, preferably sodium hydroxide.

The molar ratio of the alkaline reagent to compound I may be a conventional molar ratio in the art for such reactions, preferably 1-20, for example, 4.

The temperature of the reaction may be a conventional temperature in the art for such reactions, preferably 0-80° C., for example, 45° C.

The monitoring of the substitution reaction may be a conventional monitoring in the art for such reactions, for example, TLC, for another example, LC-MS. Generally, the complete disappearance of compound I is considered as the end of the reaction. The time for the reaction is preferably 8-18 h, for example, 12 h.

After the reaction is completed, the method may further comprise the following post-treatment steps: cooling the reaction solution after the reaction to room temperature, adjusting pH of the reaction solution to 5-6, filtering, and drying.

The present invention further provides a method for preparing a compound of formula YY-20394, comprising:

step S1: in the action of a palladium catalyst and an alkaline reagent, performing a Suzuki reaction of compound S and compound IV as represented by the following formula in a solvent to obtain compound V;

step S2: in the action of an alkaline reagent, performing a reaction of methylsulfonyl chloride and compound V as represented by the following formula in an organic solvent to obtain compound VI;

step S3: in the action of an alkaline reagent and in the presence of a palladium catalyst and a ligand, performing a conjugation reaction of compound VII and compound VI as represented by the following formula in a solvent to obtain compound YY-20394;

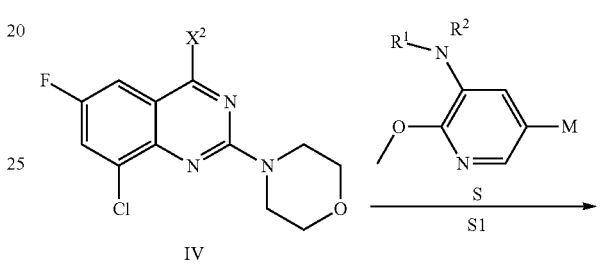

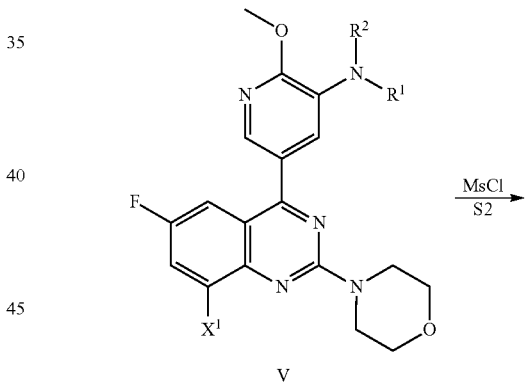

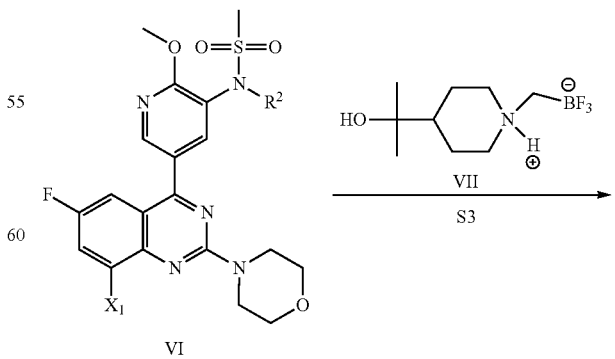

-continued

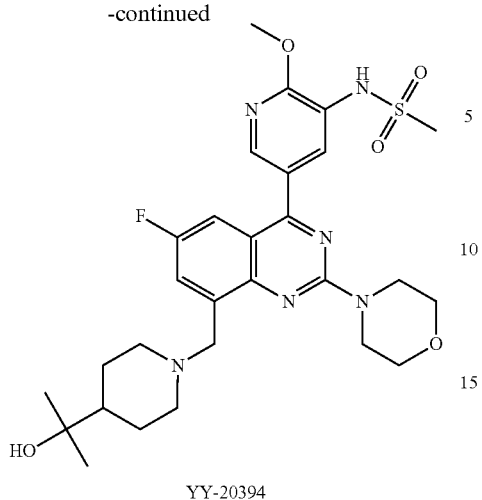

YY-20394 wherein $X^1$, $X^2$, $R^1$ and $R^2$ are as defined above; when $R^1$ and $R^2$ in compound V are both

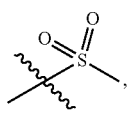

compound V is directly subjected to the conjugation reaction in step S3 without step S2; the conditions and procedures of the method for preparing compound V are as defined above.

In the method for preparing the compound of formula YY-20394, when $R^1$ and $R^2$ in compound V are not both H or

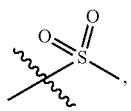

compound V is directly subjected to the conjugation reaction in step S3 without step S2.

In step S2, the reaction conditions may be conventional reaction conditions in the art for such reactions, and the following conditions are preferable in the present invention:

In step S2, the alkaline reagent is preferably a weak organic alkali. The weak organic alkali may be a conventional weak organic alkali in the art for such reactions. The weak organic alkali may be a pyridine weak organic alkali and/or a tertiary amine weak organic alkali, preferably a pyridine weak organic alkali. The pyridine weak organic alkali may be pyridine.

In step S2, the molar ratio of methylsulfonyl chloride to compound V may be 1-5, for example, 2.

In step S2, the molar ratio of the alkaline reagent to compound V may be 3-25, for example, 23.

In step S2, the organic solvent is preferably a chlorinated hydrocarbon solvent. The chlorinated hydrocarbon solvent is preferably dichloromethane.

In step S2, the reaction temperature may be 10-50° C.

In step S2, the monitoring of the reaction may be a conventional monitoring in the art for such reactions, for example, TLC, for another example, LC-MS. Generally, the complete disappearance of compound V is considered as the end of the reaction. The time for the reaction is preferably 1-24 h.

In step S2, compound V is preferably

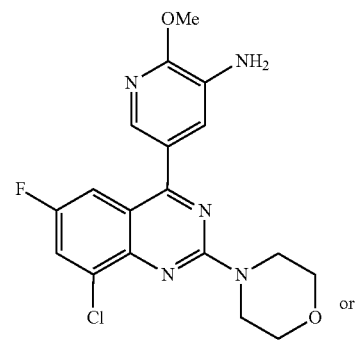
V-11 or

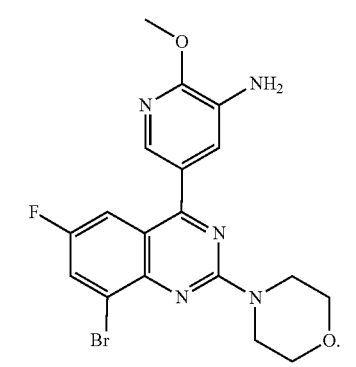
V-21

In step S2, after the reaction is completed, the method may further comprise the following post-treatment steps: quenching the reaction after the reaction, filtering, and resuspending.

In step S3, the conjugation reaction may be a conventional reaction in the art.

In step S3, the palladium catalyst may be a conventional palladium catalyst in the art for such reactions, preferably one or more of tetrakis(triphenylphosphine)palladium (Pd(PPh$_3$)$_4$), palladium acetate Pd(OAc)$_2$, bis(triphenylphosphine)palladium dichloride (PdCl$_2$ (PPh$_3$)$_2$), dichlorobis(tri-o-tolylphosphine)palladium(II) (PdCl$_2$[P(o-tol)$_3$]$_2$), tris(dibenzylideneacetone) dipalladium (Pd$_2$(dba)$_3$), bis(tri-tert-butylphosphine)palladium (Pd[P(t-Bu)$_3$]$_2$), [1,1□] bis(diphenylphosphino)ferrocene]palladium dichloride (PdCl$_2$(dppf)) and [1,1□] bis(diphenylphosphino)ferrocene]palladium(II)dichloride dichloromethane complex (PdCl$_2$(dppf)DCM), preferably palladium acetate.

In step S3, the molar ratio of the palladium catalyst to compound VI may be 0.01-0.2, for example, 0.1.

In step S3, the ligand may be a conventional ligand in the art for such reactions, preferably one or more of triphenylphosphine (PPh$_3$), tris(o-tolyl)phosphine (P(o-tol)$_3$), tri-tert-butylphosphine tetrafluoroborate, 2-dicyclohexylphosphino-2□,4□,6□-triisopropylbiphenyl (x-Phos), 2-dicyclohexylphosphino-2□,6□-dimethoxy-biphenyl (s-Phos) and 2-dicyclohexylphosphino-2□,6□-diisopropoxy-1,1'-biphenyl (Ru-Phos), preferably 2-dicyclohexylphosphino-2□,4□,6□-triisopropylbiphenyl.

In step S3, the molar ratio of the ligand to compound VI may be 0.02-0.4, for example, 0.2.

In step S3, the alkaline reagent may be a conventional alkaline reagent in the art for such reactions, preferably one or more of alkali metal carbonate, alkali metal fluoride, alkali metal phosphate, alkali metal tert-butoxide and alkali metal hydroxide. The alkali metal carbonate may be one or more of sodium carbonate, potassium carbonate and cesium carbonate, preferably potassium carbonate ($Cs_2CO_3$). The alkali metal fluoride may be potassium fluoride. The alkali metal phosphate may be potassium phosphate. The alkali metal tert-butoxide may be sodium tert-butoxide and/or potassium tert-butoxide. The alkali metal hydroxide may be one or more of sodium hydroxide, potassium hydroxide and lithium hydroxide.

In step S3, the molar ratio of the alkaline reagent to compound V may be 1-20, for example 3; for another example, 6; for still another example, 10, for further still another example, 15, for even further still another example, 20.

In step S3, the molar ratio of compound VII to compound VI may be 0.8-6, preferably 1-3, for example, 5, for another example, 1.5.

In step S3, the solvent may be a conventional solvent in the art for such reactions, preferably a mixed solvent of a water-soluble organic solvent and water. The water-soluble organic solvent may be a conventional water-soluble organic solvent in the art for such reactions. The water-soluble organic solvent is preferably an ether solvent and/or an alcohol solvent, more preferably an ether solvent. The ether solvent is preferably one or more of tetrahydrofuran (THF), 1,4-dioxane and ethylene glycol dimethyl ether, more preferably tetrahydrofuran. The volume ratio of the organic solvent to water may be a conventional volume ratio in the art, preferably 1:1-15:1, more preferably 3:1-15:1, for example, 10:1, for another example, 4:1.

In step S3, the conjugation reaction may be performed in a conventional manner in the art for such reactions, for example, by a conventional heating procedure or in a microwave condition.

When the conjugation reaction is performed by a conventional heating procedure, the temperature of the conjugation reaction may be 30-130° C., preferably 80-120° C. The time for the conjugation reaction may be 2-16 h, for example, 12 h.

When the conjugation reaction is performed in a microwave condition, the temperature of the conjugation reaction may be 50-120° C. The time for the conjugation reaction may be 5-16 h, for example, 8 h, for another example, 12 h.

In step S3, compound VI is preferably

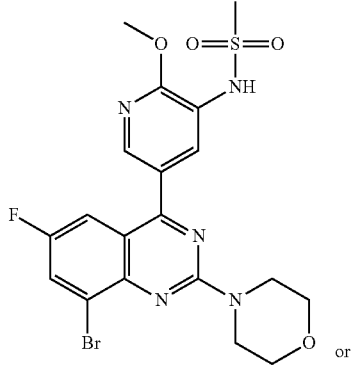

VI-11

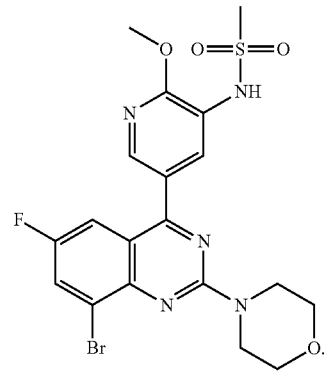

VI-21

In step S3, the conjugation reaction may also be performed in a protective gas atmosphere. The protective gas may be a conventional protective gas in the art, for example, nitrogen, for another example, argon.

In step S3, after the conjugation reaction is completed, the method may further comprise the following post-treatment steps: extracting the reaction solution after the reaction, washing, concentrating, and performing column chromatography.

The present invention further provides a compound of formula IV:

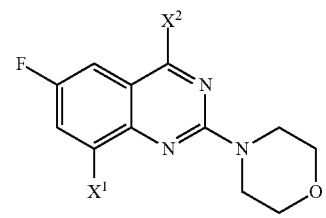

IV wherein $X^1$ and $X^2$ are as defined above.

Compound IV is preferably

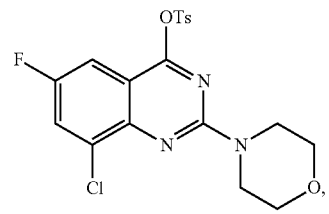

IV-11

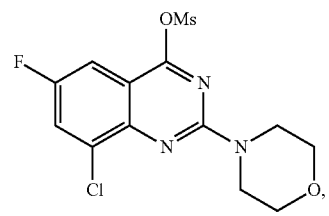

IV-12

-continued

IV-13
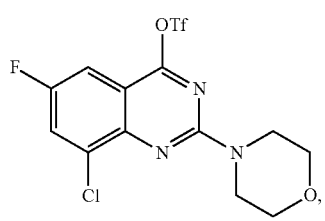

IV-14
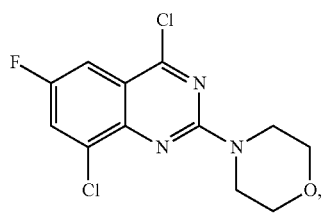

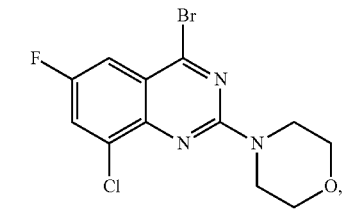

IV-21
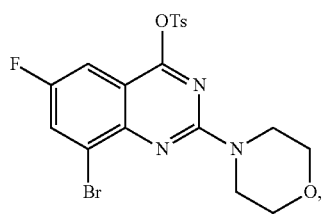

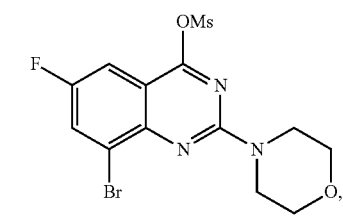

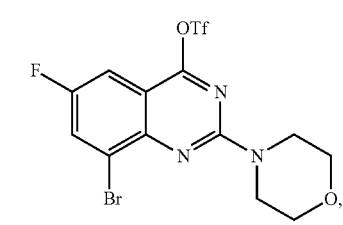

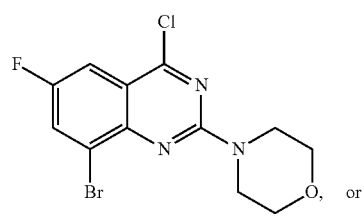 or

-continued

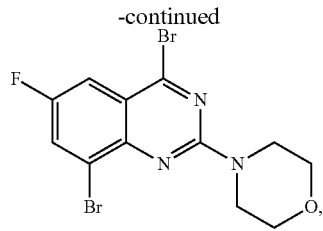

more preferably

IV-11
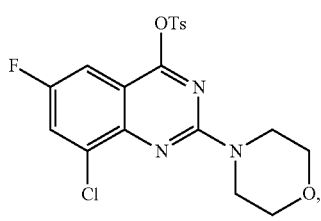

IV-12
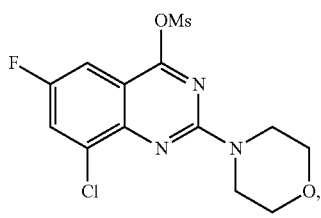

IV-13
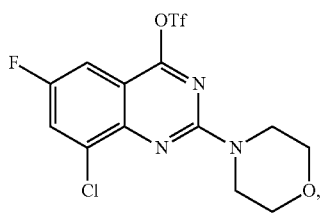

IV-14
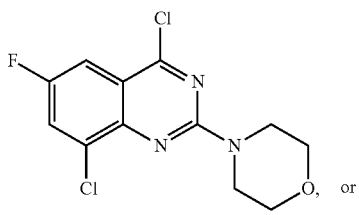, or

IV-21
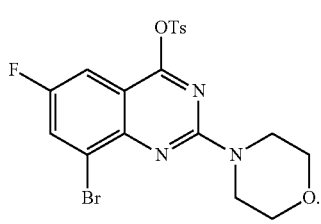.

The present invention further provides a method for preparing the compound of formula V, comprising method 1 and method 2:

method 1 comprising: performing a halogenation reaction of compound III and "phosphorus oxyhalide and/or phosphorus halide" as represented by the following formula to obtain compound IV;

method 2 comprising: in the action of an alkaline reagent, performing a nucleophilic substitution reaction of compound III and a sulfonation reagent as represented by the following formula in an organic solvent to obtain compound IV; the sulfonation reagent is

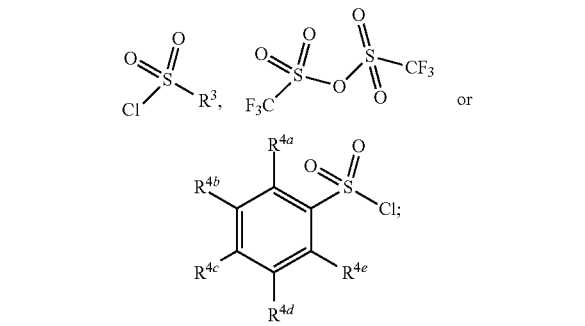

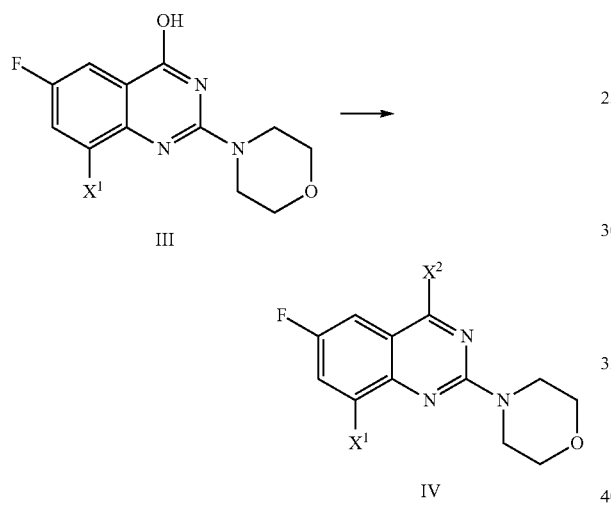

wherein $R^3$, $R^{4a}$, $R^{4b}$, $R^{4c}$, $R^{4d}$, $R^{4e}$, $X^1$ and $X^2$ are as defined above;

when $X^2$ is halogen, the method for preparing compound IV is method 1;

when $X^2$ is

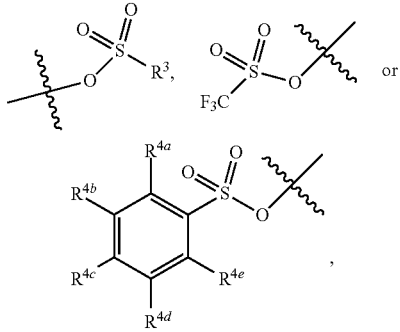

the method for preparing compound IV is method 2.

In the above reaction, the conditions for method 1 and method 2 are as defined above.

The present invention further provides compound III:

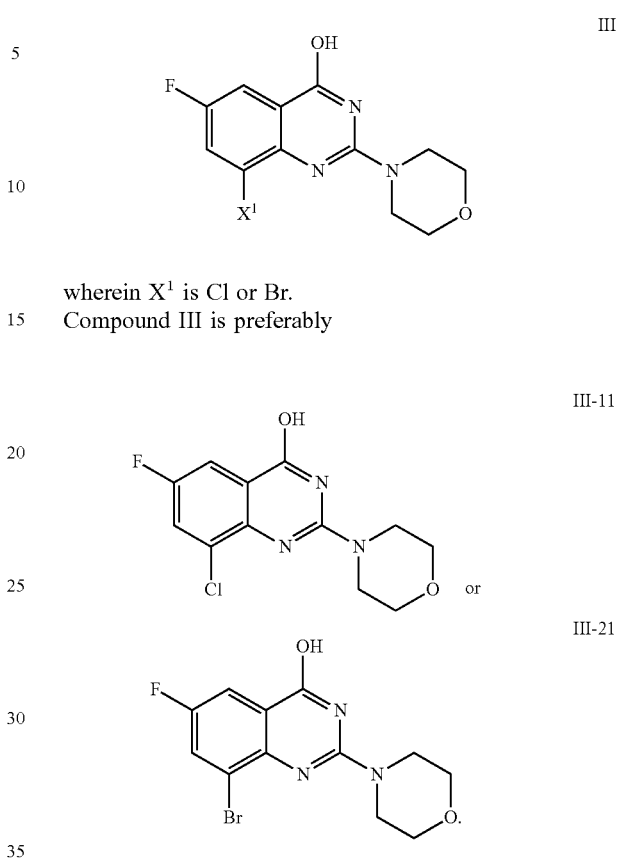

wherein $X^1$ is Cl or Br.

Compound III is preferably

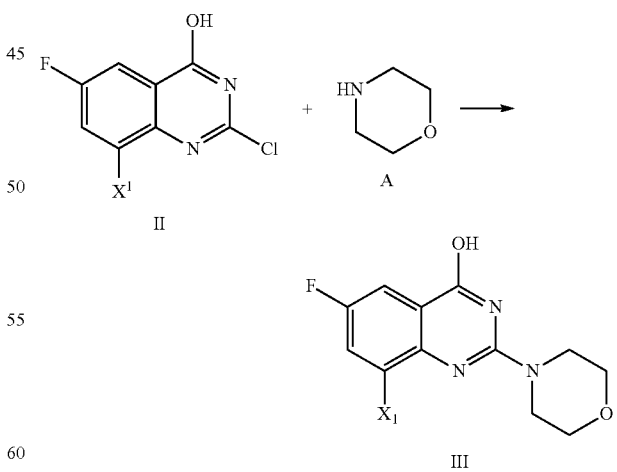

The present invention further provides a method for preparing compound III, comprising: performing a nucleophilic substitution reaction of compound II and compound A as represented by the following formula in an organic solvent to obtain compound III;

wherein $X^1$ is Cl or Br.

The conditions of the nucleophilic substitution reaction are as defined above.

The present invention further provides a compound of formula II:

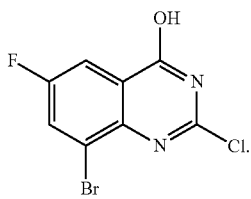

II

The present invention further provides a compound of formula V-2:

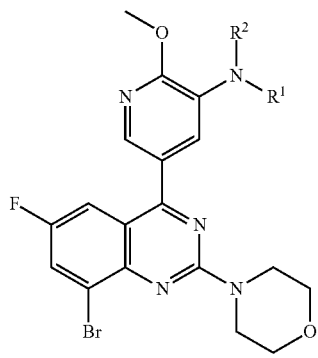

V-2 wherein $R^1$ and $R^2$ are independently H or

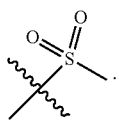

Compound V-2 is preferably

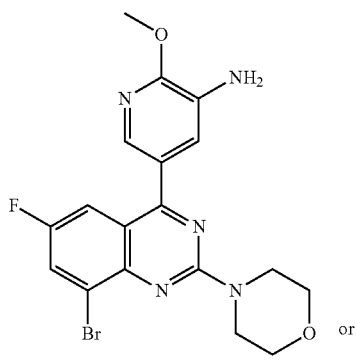

V-21 or

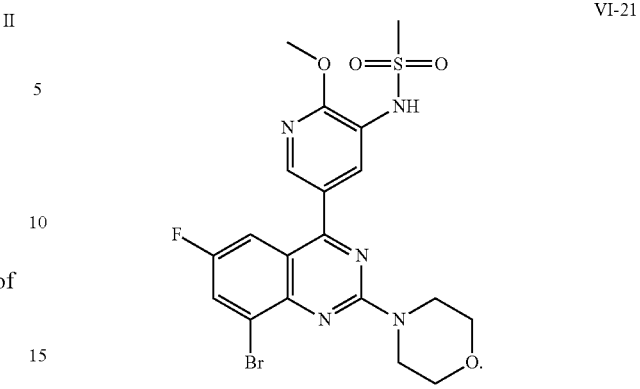

VI-21

The methods for preparing the above compounds may be combined as desired to obtain synthetic routes to compounds of formula III, IV, V or YY-20394 (e.g., I→II→III→V→VI→YY-20394, II→III→IV→V→VI→YY-20394, I→II→III→IV→V, I→II→III→IV, II→III→IV, I→II→III).

In the present invention, the following abbreviations are used:

THF=tetrahydrofuran; t-Bu=tert-butyl; DCM=dichloromethane; NCS=N-chlorosuccinimide; Ts=p-toluenesulfonyl; Ns=p-nitrotoluenesulfonyl; Ms=methanesulfonyl; Tf=trifluoromethanesulfonyl; Ac=acetyl; DIPEA=diisopropylethylamine; DMF=dimethylformamide; DMAC=N,N-dimethylacetamide; DMSO=dimethylsulfoxide; dba=dibenzylideneacetone; dppf=1,1'-bis(diphenylphosphino)ferrocene; x-Phos=2-dicyclohexylphosphino-2',4',6'-triisopropylbiphenyl; s-Phos=2-dicyclohexylphosphino-2',6'-dimethoxy-biphenyl; Ru-Phos=2-dicyclohexylphosphino-2',6'-diisopropoxy-1,1'-biphenyl; g=gram; mg=milligram; mL=milliliter; mol=mole; mmol=millimole; h=hour; LCMS=liquid phase-mass spectrometry; MS=mass spectrometry; ESI=electrospray ionization; m/z=mass-to-charge ratio; $^1$H NMR=nuclear magnetic resonance; MHz=megahertz; brs=broad singlet; d=doublet; t=triplet; q=quartet; m=multiplet; dd=doublet of doublets; J=coupling constant; N=moles per liter.

As used herein, "room temperature" refers to the ambient temperature, and particularly, to 10-35° C.

As used herein, "overnight" refers to 8-16 hours.

As used herein, "water-soluble organic solvent" refers to that the solvent molecule generally contains a polar group, for example, —OH, —SO$_3$H, —NH$_2$, —NHR, —COOH, —CN, —CO— and —CONH2— groups, and a carbon backbone of 8 carbons or less. Acetone, acetonitrile and N,N-dimethylformamide are common "water-soluble organic solvents".

The above preferred conditions may be combined arbitrarily to obtain preferred embodiments of the present invention without departing from the general knowledge in the art.

The reagents and starting materials used in the present invention are commercially available.

The advantageous effects of the present invention are as follows: the method for preparing the morpholinyl quinazoline compound disclosed herein features increased selectivity of the Suzuki reaction at position 4 of the quinazoline ring to solve the problem of considerable byproducts of the reactions, high yield, ease-to-operate and mild reaction conditions, and is suitable for industrial manufacture.

DETAILED DESCRIPTION

The present invention is further illustrated by the following examples, which are not intended to limit the present invention. Experimental procedures without specified conditions in the following examples were performed in accordance with conventional procedures and conditions, or in accordance with instructions.

Example 1. Synthesis of Compound I-11

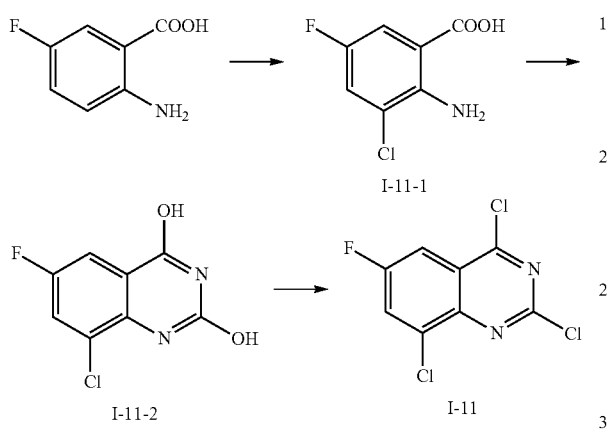

2-Amino-5-fluorobenzoic acid (100.2 g, 0.65 mol) was dissolved in DMF (600 mL), and the mixture was added with NCS (104.5 g, 0.78 mol) in portions while stirring at room temperature. After the addition was completed, the mixture was stirred at room temperature overnight. Water (1200 mL) was added to the reaction solution to precipitate solids. The mixture was filtered, and the filter cake was washed with water, dried, and resuspended in dichloromethane. The mixture was filtered, and the residues were dried to obtain compound I-11-1 (85.1 g, 70% yield) as an off-white solid. LC-MS (ESI): m/z=190.0 [M+H]$^+$.

Compound I-11-1 (25.0 g, 0.13 mol) and urea (119.1 g, 1.98 mol) were added to a flask and the mixture was incubated at 180° C. for 8 h. The reaction solution was cooled to about 100° C. and water was added for 2 h of resuspension. The mixture was filtered, and the filter cake was resuspended in water, filtered and dried twice to obtain compound 1-11-2 (26.7 g, 94% yield) as a brown solid. LC-MS (ESI): m/z=215.0 [M+H]$^+$.

Compound 1-11-2 (20.0 g, 0.093 mol) and phosphorus oxychloride (160 g, 1.04 mol) were added to a flask before DIPEA (24.0 g, 0.19 mol) was added dropwise below 50° C. After the addition was completed, the mixture was incubated at 110° C. for 2 h. The reaction solution was concentrated and washed with toluene twice. A small amount of toluene was then slowly & dropwise added to aqueous phase, with the temperature controlled at 40° C. or less. After the addition was completed, the mixture was continuously stirred for 0.5 h and separated. The aqueous phase was extracted with toluene. The toluene phases were combined, washed with saturated sodium chloride, dried over anhydrous magnesium sulfate and concentrated. The residues were resuspended in n-heptane, filtered, and dried to obtain compound I-11 (19.9 g, 85% yield) as an off-white solid. LC-MS (ESI): m/z=251.1 [M+H]$^+$.

Example 2. Synthesis of Compound II-11

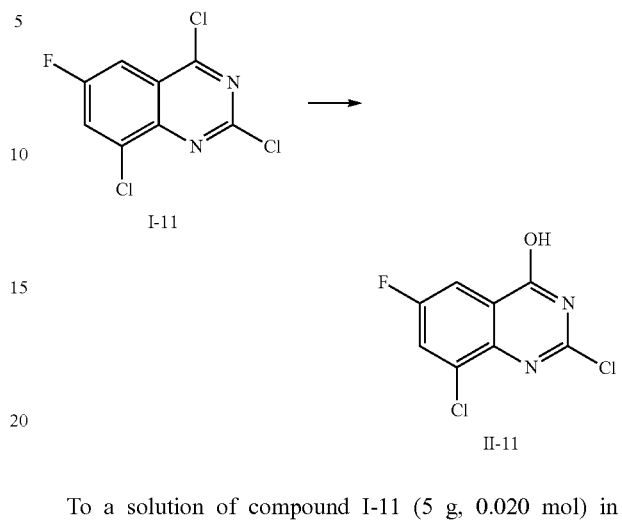

To a solution of compound I-11 (5 g, 0.020 mol) in acetonitrile (70 mL), an aqueous sodium hydroxide solution (2 N, 40 mL) was added at room temperature. After the addition was completed, the reaction solution was stirred at 45° C. overnight. The reaction solution was cooled to room temperature, and then transferred to an ice-water bath before an aqueous hydrochloric acid solution (2 N, 42 mL) was slowly added to adjust the pH to 5-6. A solid was precipitated. The mixture was filtered, and the filter cake was washed with water and dried to obtain compound II-11 (4.1 g, 89% yield) as an off-white solid. LC-MS (ESI): m/z=232.9 [M+H]$^+$; $^1$H NMR (400 MHz, DMSO-d$_6$): δ 13.63 (brs, 1H), 8.06 (dd, 1H, J=2.8, 8.4 Hz), 7.78 (dd, 1H, J=2.8, 8.0 Hz).

Example 3. Synthesis of Compound III-11

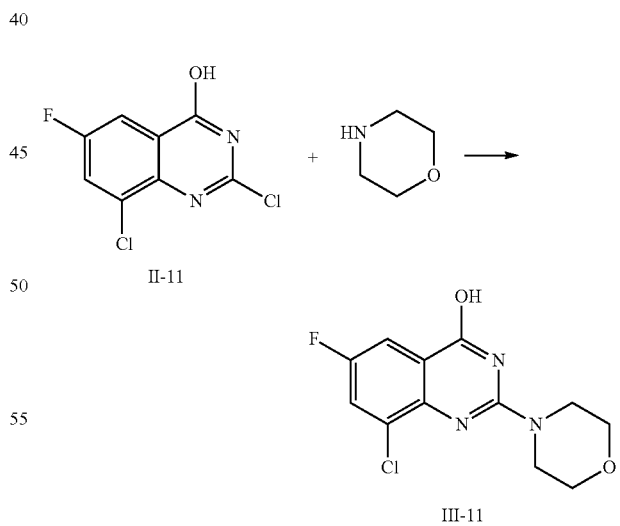

To a solution of compound II-11 (3 g, 0.013 mol) in DMAC (30 mL), morpholine (2.7 g, 0.031 mol) was added at room temperature. After the addition was completed, the reaction solution was stirred at 85° C. for 2 h. The reaction solution was cooled to room temperature, and then transferred to an ice-water bath before water (70 mL) was slowly added. A solid was precipitated. The mixture was filtered, and the filter cake was washed with water and dried to obtain compound III-11 (3.2 g, 88% yield) as a pale yellow solid. LC-MS (ESI): m/z=284.1[M+H]⁺; ¹H NMR (400 MHz, DMSO-d₆): δ 11.69 (brs, 1H), 7.81 (dd, J=8.4 Hz, 2.8 Hz 1H), 7.59 (dd, J=8.0 Hz, 2.8 Hz 1H), 3.55-3.80 (m, 8H).

Example 4. Synthesis of Compound IV-11

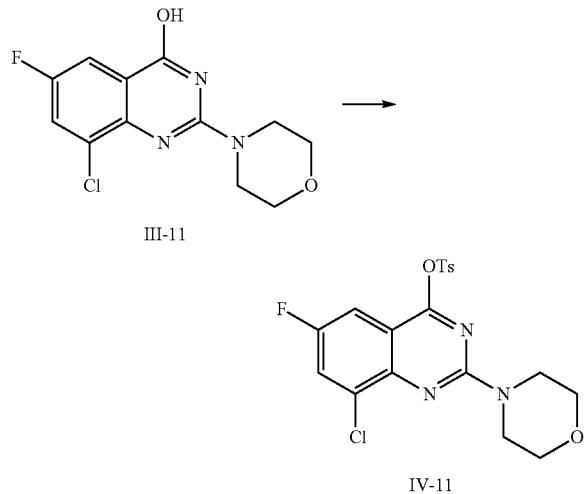

To a solution of compound III-11 (36.0 g, 0.13 mol) in acetonitrile (360 mL), potassium carbonate (24 g, 0.17 mol) and p-toluenesulfonyl chloride (24.0 g, 0.13 mol) were added at room temperature. After the addition was completed, the reaction solution was stirred at 80° C. for 2 h. The reaction solution was cooled to room temperature, transferred to an ice-water bath, and dropwise added with water with the temperature controlled at 25° C. or less. After the addition was completed, the mixture was continuously stirred for 1 h. The mixture was filtered, and the filter cake was washed with water and dried to obtain compound IV-11 (48 g, 86% yield) as a yellow solid. LC-MS (ESI): m/z=438.0 [M+H]⁺.

Example 5. Synthesis of Compound V-11

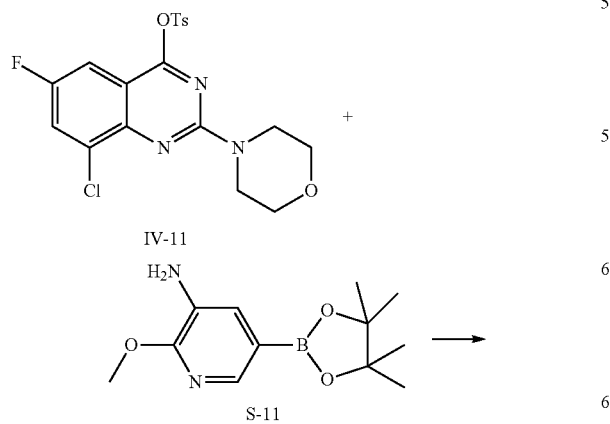

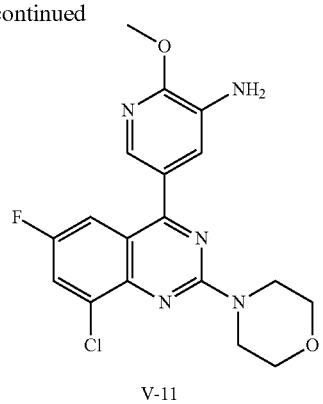

To a flask, the compounds IV-11 (157.0 g, 0.36 mol) and 5-11 (81.5 g, 0.33 mol), sodium carbonate (345.5 g, 3.26 mol), toluene (3.5 L), isopropanol (1.2 L) and water (1.6 L) were added. The reaction system was purged with nitrogen three times, and tetrakis(triphenylphosphine)palladium (18.8 g, 0.016 mol) was added in nitrogen atmosphere. After the addition was completed, the reaction solution was stirred at 35-40° C. for 1 h. The reaction solution was cooled to room temperature and separated. The aqueous phase was extracted with toluene. The toluene phases were combined, concentrated to some extent, added with n-heptane, filtered and purified by silica gel column chromatography to obtain compound V-11 (115 g, 91% yield) as a yellow solid. ¹H NMR (400 MHz, CDCl₃): δ 7.94 (d, J=2.8 Hz, 1H), 7.63 (dd, J=8.0 Hz, 2.8 Hz, 1H), 7.55 (dd, J=9.2 Hz, 2.8 Hz, 1H), 7.24-7.27 (m, 1H), 4.11 (s, 3H), 3.90-4.06 (m, 6H), 3.84(t, J=5.2 Hz, 4H).

Example 6. Synthesis of Compound VI-11

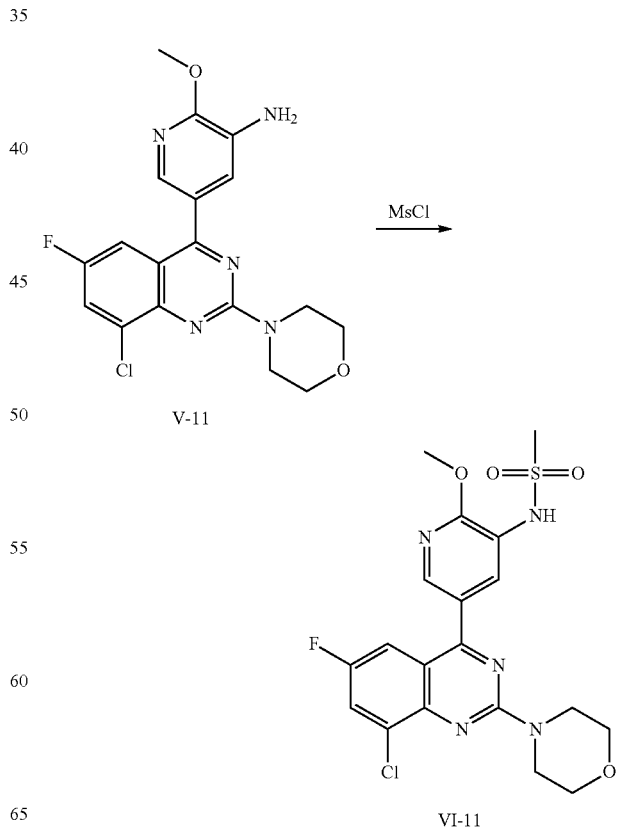

To a solution of compound V-11 (110 g, 0.28 mol) in pyridine (550 g, 6.59 mol) in an ice-salt bath, methanesulfonyl chloride (63.8 g, 0.56 mol) was added dropwise. After the addition was completed, the reaction solution was stirred at room temperature until the reaction was completed. The reaction solution was carefully added with water (1100 mL) and filtered, and the filter cake was washed with water, dried, resuspended in dichloromethane, filtered, and dried to obtain compound VI-11 (105.0 g, 80% yield) as a yellow solid. LC-MS (ESI): m/z=468.1 [M+H]$^+$; $^1$H NMR (400 MHz, DMSO-$d_6$): δ 9.53 (s, 1H), 8.43 (d, J=2.4 Hz, 1H), 8.07 (dd, J=11.2 Hz, 2.4 Hz; 1H), 8.03 (d, J=2.4 Hz, 1H), 7.57(dd, J=9.2 Hz, 2.4 Hz; 1H), 4.04 (s, 3H), 3.92-3.86 (m, 4H), 3.74-3.72 (m, 4H),.3.12(s, 3H).

Example 7. Synthesis of Compound VI-11

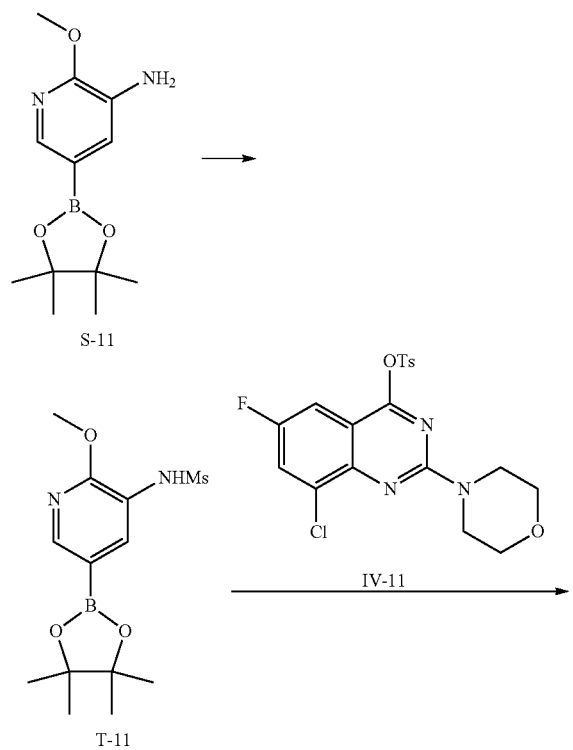

To a solution of compound S-11 (2.0 g, 8 mmol) in pyridine (20 mL) at 0-10° C., methanesulfonyl chloride (1.24 mL, 16.0 mmol) was slowly & dropwise added, and after the addition was completed, the reaction solution was stirred at room temperature overnight. The reaction solution was concentrated to remove pyridine, and saturated aqueous sodium bicarbonate (20 mL) and dichloromethane (40 mL) were added to the residues. The mixture was separated, and the aqueous phase was extracted with dichloromethane. The organic phases were combined, washed with saturated aqueous sodium chloride, dried over anhydrous sodium sulfate, and concentrated to obtain compound T-11 (4.29 g, 100% yield) as a yellow oil. LC-MS (ESI): m/z=329.2 [M+H]$^+$.

To a flask, the compounds T-11 [352 mg, 0.65 mmol (61% purity)] and IV-11 (281 mg, 0.64 mmol), sodium carbonate (0.102 g, 0.96 mmol), tetrakis(triphenylphosphine) palladium(0) (74 mg, 0.064 mmol) and a mixture of toluene/isopropanol/water (volume ratio=4/1/1, 8 mL) were added. After the addition was completed, the reaction system was purged with nitrogen and stirred at 60° C. for 4 h. The reaction solution was concentrated and the residues were extracted with dichloromethane. The organic phase was washed with saturated aqueous sodium chloride, dried over anhydrous sodium sulfate and concentrated. The residues were resuspended in dichloromethane and filtered to obtain compound VI-11 (170 mg, 53% yield) as a yellow solid. LC-MS (ESI): m/z=468.1 [M+H]$^+$.

Example 8. Synthesis of Compound VII-11

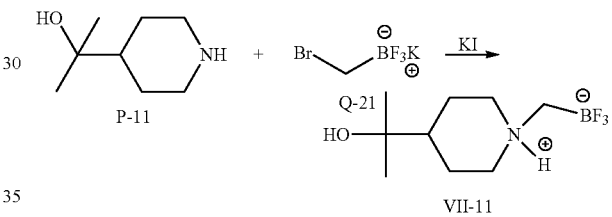

To a flask, the compounds P-11 (100 g, 0.70 mol) and Q-21 (127.5 g, 0.63 mol), acetonitrile (100 g) and potassium iodide (6 g, 0.036 mol) were added. After the addition was completed, the reaction solution was stirred at 80° C. overnight. The reaction solution was concentrated, and the residues were resuspended in hot acetonitrile, filtered and dried to obtain compound VII-11 (140.0 g, 98%) as an off-white solid. $^1$H NMR (400 MHz, D20): δ 3.51 (d, J=12.8 Hz, 2H), 2.80 (t, J=12.8 Hz, 2H), 2.05-2.22 (m, 2H), 1.90 (d, J=13.2 Hz, 2H), 1.40-1.62 (m, 3H), 1.12 (s, 6H).

Example 9. Synthesis of Compound YY-20394

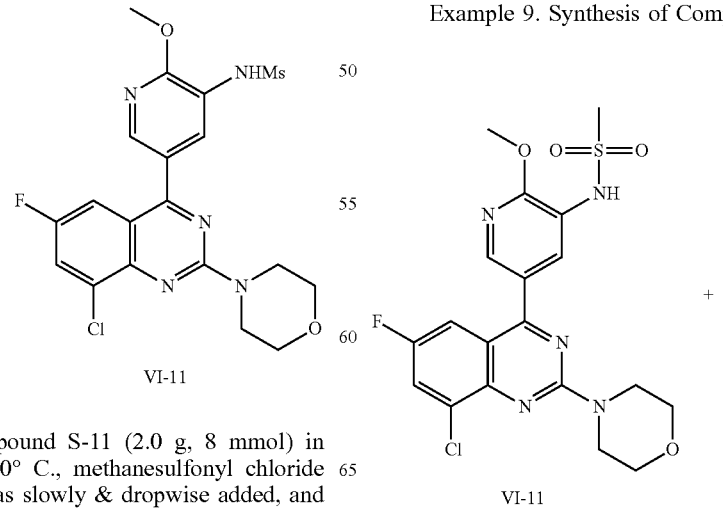

31

-continued

VII-11

→

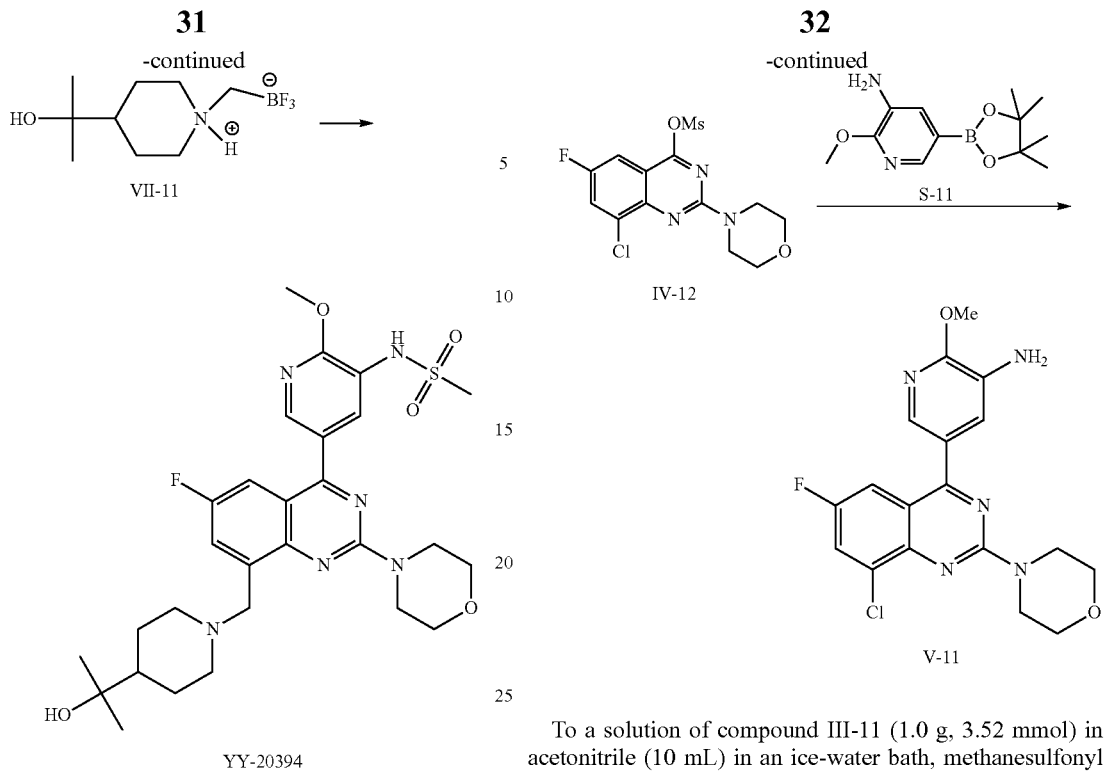

YY-20394

To a flask, the compounds VI-11 (35 g, 0.075 mol) and VII-11 (34 g, 0.15 mol), cesium carbonate (244 g, 0.75), x-Phos (3.55 g, 0.0074 mol), and a mixture of THF and water (10/1 v/v, 385 mL) and palladium acetate (0.84 g, 0.0037 mol) were added at room temperature. The mixture was purged with nitrogen three times and stirred at 80° C. overnight. The reaction solution was cooled to room temperature and concentrated to remove THF, and the residues were extracted with DCM. The organic phase was washed with saturated sodium chloride, dried over anhydrous sodium sulfate, concentrated and purified by silica gel column chromatography. The crude product was resuspended in ethanol, filtered and dried to obtain compound YY-20394 (26 g, 59% yield) as a yellow solid. LC-MS (ESI): m/z=589.3 [M+H]$^+$; $^1$H NMR (500 MHz, DMSO-d$_6$) δ .53(brs, 1H), 8.35(d, J=2.0 Hz, 1H), 8.01(d, J=2.4 Hz, 1H), 7.61(dd, J=9.6 Hz, 2.4 Hz, 1H), 7.39(dd, J=9.6 Hz, 2.4 Hz, 1H), 4.05(s, 4H), 3.87(s, 2H), 3.82-3.81(m, 4H), 3.73-3.72 (m, 4H), 3.13(s, 3H), 2.94(d, J=10.8 Hz, 1H), 2.04-1.98(m, 2H), 1.66(d, J=11.6 Hz, 2H), 1.36-1.64(m, 2H), 1.21-1.18 (m, 1H), 1.21-1.18(m, 1H), 1.04(s, 6H).

Example 10. Synthesis of Compound V-11

32

-continued

IV-12  →  S-11

V-11

To a solution of compound III-11 (1.0 g, 3.52 mmol) in acetonitrile (10 mL) in an ice-water bath, methanesulfonyl chloride (0.55 mL, 7.06 mmol) and DIPEA (1.33 mL, 7.76 mmol) were added dropwise in sequence. After the addition was completed, the mixture was stirred at room temperature for 2 h. The reaction solution was added with ice-water (15 mL), stirred for 10 min, and filtered. The filter cake was washed with water and dried to obtain compound IV-12 (3.01 g, 100% yield).

To a flask, the compounds IV-12 (3.01 g, 3.52 mmol) and 5-11 (0.88 g, 3.52 mmol), sodium carbonate (0.56 g, 5.30 mmol), tetrakis(triphenylphosphine)palladium (408 mg, 0.353 mmol) and a mixture of toluene/isopropanol/water (volume ratio=4/1/1, 15 mL) were added at room temperature. After the addition was completed, the reaction system was purged with nitrogen, and stirred at 30° C. for 2 h and then at 45° C. overnight. The reaction solution was concentrated, and dichloromethane (40 mL) and water (20 mL) were added to the residues. The mixture was separated, and the aqueous phase was extracted with dichloromethane. The organic phases were combined, washed with saturated aqueous sodium chloride, dried over anhydrous sodium sulfate, concentrated, and purified by silica gel column chromatography to obtain compound V-11 (1.02 g, 74% yield) as a yellow solid. LC-MS (ESI): m/z=390.2 [M+H]$^+$.

Example 11. Synthesis of Compound V-11

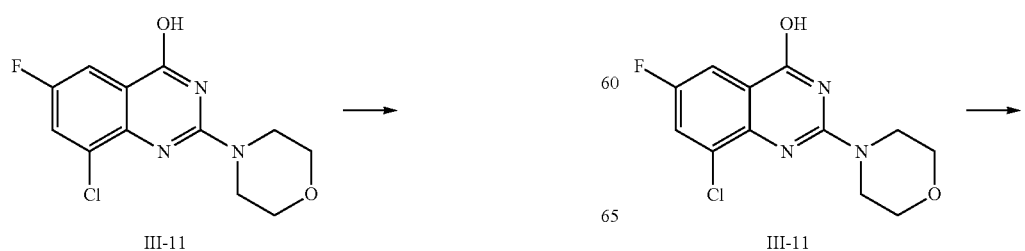

-continued

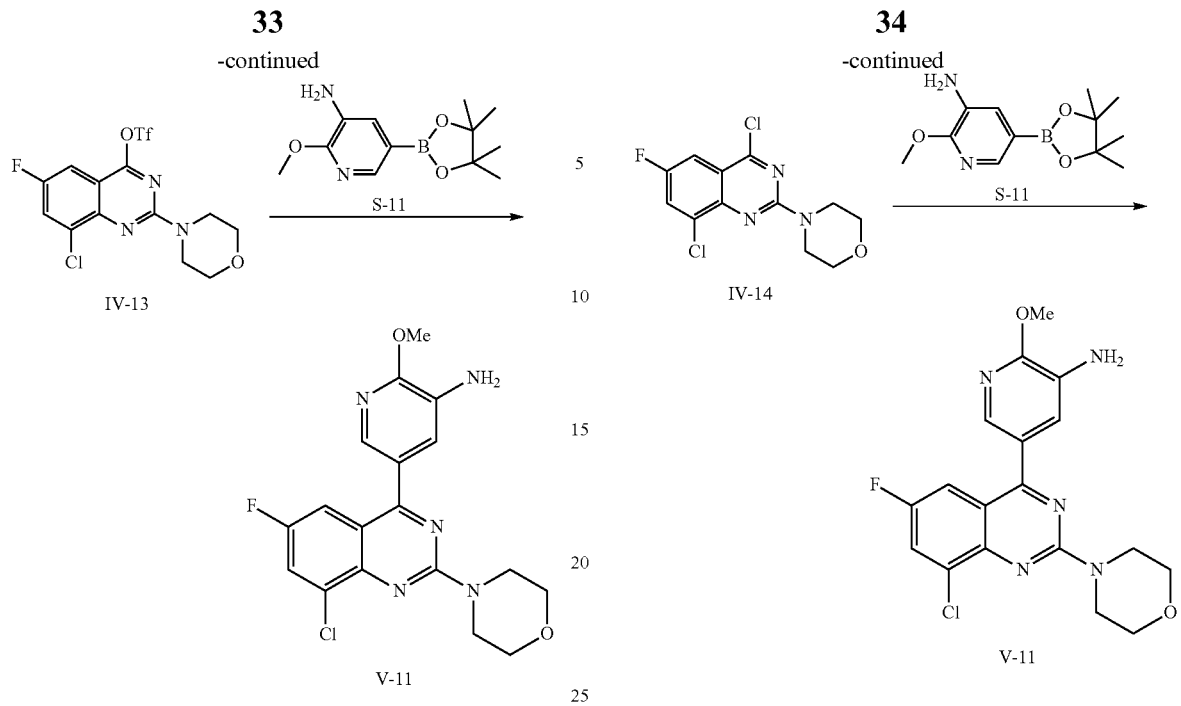

To a solution of compound III-11 (0.28 g, 0.99 mmol) in dichloromethane (10 mL) in an ice-water bath, DIPEA (0.26 g, 2.0 mmol) was added before trifluoromethanesulfonic anhydride (0.56 g, 2.0 mmol) was added dropwise. After the addition was completed, the mixture was stirred for 2 h in an ice-water bath. The reaction solution was added with ice water (20 mL), and extracted with dichloromethane (20 mL×3). The organic phase was dried over anhydrous sodium sulfate and concentrated to obtain compound IV-13 (0.18 g, 44% yield) as a brown solid. LC-MS (ESI): m/z=416.1 [M+H]⁺.

To a flask, the compounds IV-13 (0.18 g, 0.43 mmol) and S11 (0.2 g, 0.8 mmol), sodium carbonate (0.1 g, 1.0 mmol), tetrakis(triphenylphosphine)palladium (33 mg, 0.028 mmol) and a mixture of toluene/isopropanol/water (volume ratio=4/1/1, 6 mL) were added at room temperature. After the addition was completed, the reaction system was purged with nitrogen, and stirred at 70° C. for 6 h. The reaction solution was concentrated, added with ethyl acetate (8 mL) and filtered. The filtrate was concentrated and purified by preparative TLC (petroleum ether/ethyl acetate=1/1) to obtain compound V-11 (0.09 g, 53% yield). LC-MS (ESI): m/z=390.1 [M+H]⁺.

Example 12. Synthesis of Compound V-11

A mixture of compound III-11 (1.0 g, 3.52 mmol) in phosphorus oxychloride (10 mL) was stirred at 105° C. for 3 h. The reaction solution was concentrated, and washed twice with toluene. The residues were added with ice water (15 mL), and the mixture was stirred for 10 min and extracted with dichloromethane. The organic phase was washed with saturated aqueous sodium chloride and concentrated to obtain compound IV-14 (1.13 g, 100% yield) as a yellow solid.

To a flask, the compounds IV-14 (1.13 g, 3.52 mmol) and S-11 (0.97 g, 3.88 mmol), sodium carbonate (0.66 g, 6.23 mmol), tetrakis(triphenylphosphine)palladium (408 mg, 0.353 mmol) and a mixture of toluene/isopropanol/water (volume ratio=4/1/1, 60 mL) were added at room temperature. After the addition was completed, the reaction system was purged with nitrogen, and stirred at 80° C. overnight. The reaction solution was concentrated, and dichloromethane (50 mL) and water (20 mL) were added to the residues. The mixture was separated, and the aqueous phase was extracted with dichloromethane. The organic phases were combined, washed with saturated aqueous sodium chloride, dried over anhydrous sodium sulfate, concentrated, and purified by silica gel column chromatography to obtain compound V-11 (1.21 g, 88% yield) as a yellow solid. LC-MS (ESI): m/z=390.2 [M+H]⁺.

Example 13. Synthesis of Compound VI-11

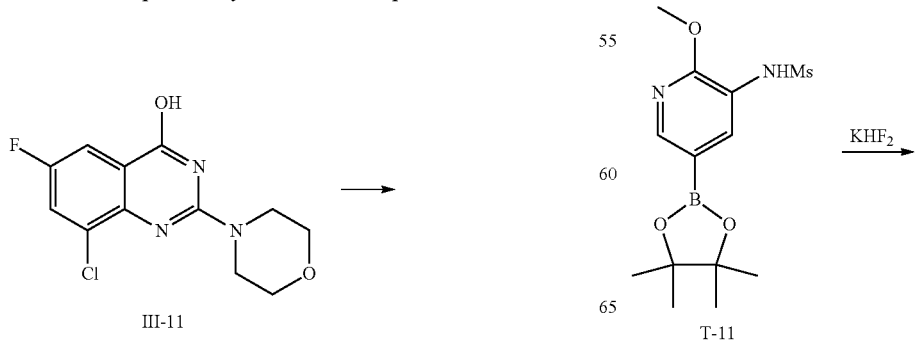

-continued

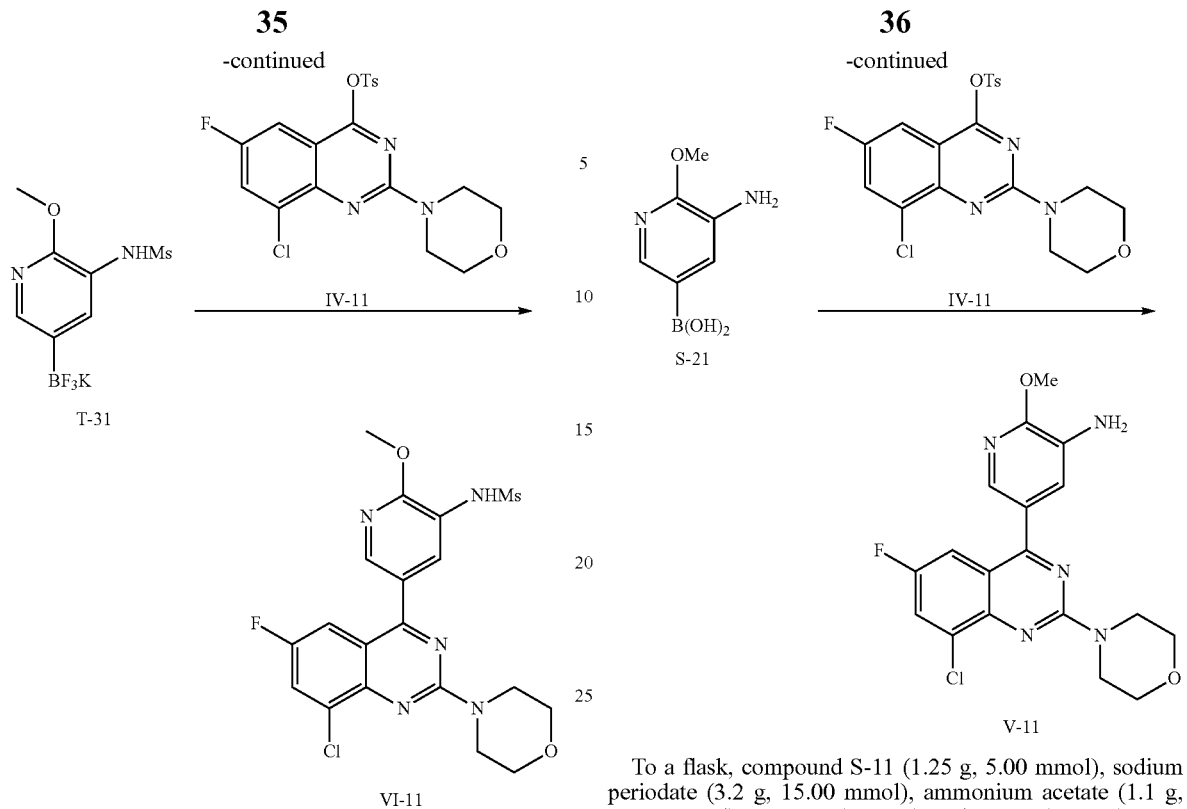

To a flask, compound T-11 [520 mg, 0.97 mmol (61% purity, the same as in Example 7)], potassium bifluoride (494 mg, 6.34 mmol) and a mixture of 1,4-dioxane/water (10/1, 4 mL) were added at room temperature. After the addition was completed, the mixture was stirred at room temperature for 1 h. The reaction solution was filtered, and the filter cake was washed with 1,4-dioxane. The filtrates were combined, concentrated, and dried to obtain compound T-31 (480 mg, 100% yield) as a pale yellow oil.

To a flask, the compounds T-31 (480 mg, 0.97 mmol) and IV-11 (395 mg, 0.90 mmol), cesium carbonate (340 mg, 1.35 mmol), palladium acetate (10 mg, 0.045 mmol), x-Phos (43 mg, 0.09 mmol) and a mixture of THF/H$_2$O (volume ratio=1/1, 8 mL) were added. The mixture was purged with nitrogen and stirred at 60° C. for 2 h. The reaction solution was concentrated and the residues were extracted with dichloromethane. The organic phase was washed with saturated aqueous sodium chloride, dried over anhydrous sodium sulfate and concentrated. The residues were resuspended in dichloromethane, filtered and dried to obtain compound VI-11 (280 mg, 62% yield). LC-MS (ESI): m/z=468.1 [M+H]$^+$.

To a flask, compound S-11 (1.25 g, 5.00 mmol), sodium periodate (3.2 g, 15.00 mmol), ammonium acetate (1.1 g, 15.00 mmol), acetone (40 mL) and water (10 mL) were added. The reaction solution was stirred at 80° C. for 12 h. After the reaction was completed, the reaction solution was concentrated, added with water (30 mL), and extracted with EA (50 mL×3). The organic phase was concentrated to obtain compound S-21 (0.66 g, 78% yield). LC-MS (ESI): m/z=169.3 [M+H]$^+$.

To a flask, the compounds IV-11 (1.2 g, 2.74 mmol) and S-21 (0.51 g, 3.04 mmol), sodium carbonate (0.4 g, 3.77 mmol), toluene (16 mL), isopropanol (4 mL) and water (4 mL) were added. After stirring and purging with nitrogen, tetrakis(triphenylphosphine) palladium(0) (0.1 g, 0.09 mmol) was added to the flask, the reaction system was purged with nitrogen again, and the mixture was incubated at 60° C. for 12 h. The reaction solution was concentrated, added with water (60 mL), filtered and dried to obtain a crude product (0.76 g). The crude product was resuspended in a mixture of petroleum ether/ethyl acetate (volume ratio=1/1; 40 mL), and purified by column chromatography (petroleum ether/ethyl acetate=1/1) to obtain compound V-11 (0.46 g, 43%). LC-MS (ESI): m/z=390.1 [M+H]$^+$.

Example 14. Synthesis of Compound V-11

Example 15. Synthesis of Compound VI-11

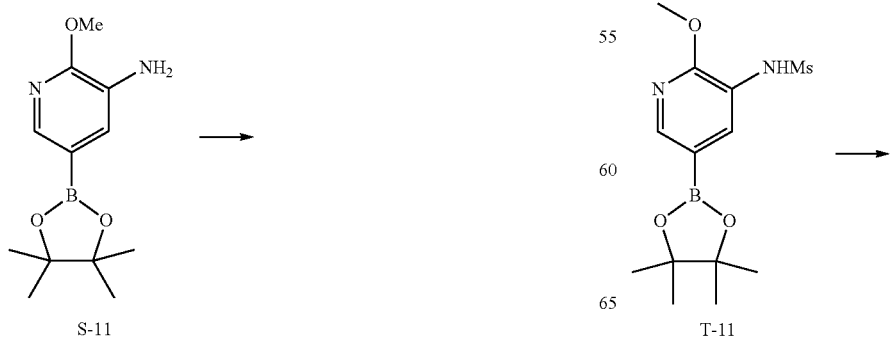

-continued

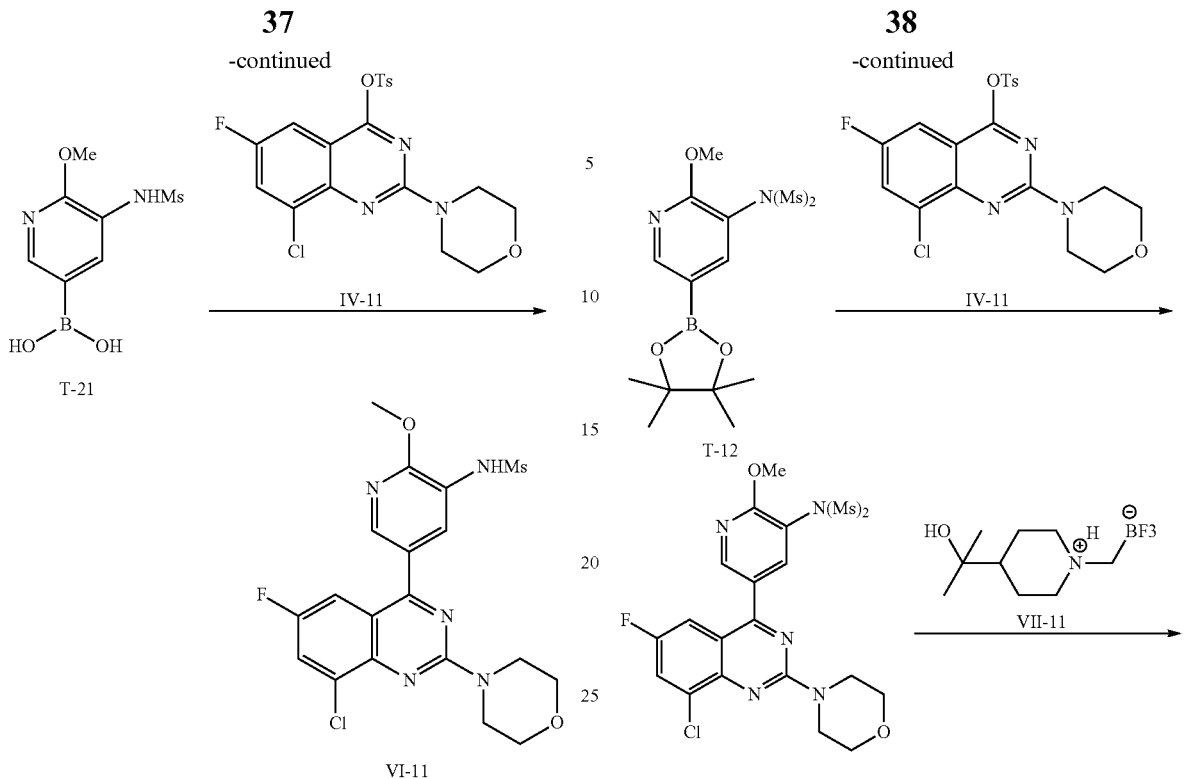

To a solution of compound T-11 (0.74 g, 2.26 mmol) in acetone (15 mL) was added a solution of sodium periodate (1.45 g, 6.78 mmol) and ammonium acetate (0.87 g, 11.3 mmol) in water (5 mL). The reaction solution was incubated at 80° C. for 12 h. After the reaction was completed, the reaction solution was concentrated to remove the solvent, added with diluted hydrochloric acid (2 N) and water, and extracted with ethyl acetate. The organic phase was concentrated to obtain compound T-21 (0.54 g, 96% yield).

To a flask, the compounds IV-11 (0.5 g, 1.14 mmol) and T-21 (423 mg, 1.72 mmol), tetrakis(triphenylphosphine) palladium (132 mg, 0.114 mmol), sodium carbonate (363 mg, 3.42 mmol), toluene (16 mL), isopropanol (4 mL) and water (4 mL) were added. The reaction system was purged with nitrogen, and incubated at 60° C. overnight. The reaction solution was concentrated by rotary evaporation, added with water, and extracted with ethyl acetate. The organic phase was washed with water, dried over anhydrous sodium sulfate and concentrated. The crude product was purified by column chromatography (DCM:MeOH=50:1-20:1) to obtain compound VI-11 (290 mg, 54% yield). LC-MS (ESI): m/z=468.1 [M+H]$^+$.

Example 16. Synthesis of Compound YY-20394

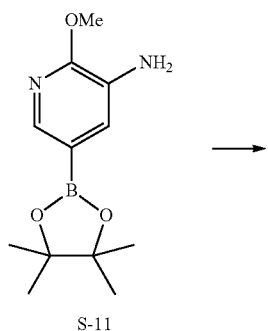

To a solution of compound 5-11 (1 g, 4.00 mmol) in dichloromethane (10 mL), triethylamine (1.2 g, 11.85 mmol) was added. MsCl (0.92 g, 8.03 mmol) was then slowly added to the reaction system in an ice-water bath. After the addition was completed, the reaction system was stirred at room temperature overnight. The reaction solution was concentrated, added with water, and extracted with ethyl acetate. The organic phase was dried over anhydrous sodium sulfate and concentrated to obtain compound T-12 (1.6 g, 98% yield).

To a flask, the compounds IV-11 (500 mg, 1.14 mmol) and T-12 (697 mg, 1.72 mmol), tetrakis(triphenylphosphine) palladium (132 mg, 0.114 mmol), sodium carbonate (363 mg, 3.42 mmol), toluene (16 mL), isopropanol (4 mL) and water (4 mL) were added. The reaction system was purged with nitrogen, and incubated at 60° C. overnight. The reaction solution was concentrated, added with water, and extracted with ethyl acetate. The organic phase was washed with water, dried over anhydrous sodium sulfate and concentrated. The crude product was purified by column chromatography (PE:EA=1:1) to obtain compound VI-12 (350 mg, 56% yield). LC-MS (ESI): m/z=546.1 [M+H]$^+$.

To a 10-mL microwave tube, the compounds VI-12 (93 mg, 0.17 mmol) and VII-11 (192 mg, 0.85 mmol), palladium acetate (4 mg, 0.017 mmol), x-Phos (16 mg, 0.034 mmol), cesium carbonate (166 mg, 0.51 mmol), THF (1.4 mL) and water (0.35 mL) were added. The microwave tube was purged with nitrogen, and incubated at 80° C. overnight. The reaction solution was concentrated, added with water, and extracted with ethyl acetate. The organic phase was washed with water, dried over anhydrous sodium sulfate and concentrated. The crude product was purified by preparative TLC (DCM:MeOH=30:1) to obtain compound YY-20394 (80 mg, 80% yield) as a yellow solid. LC-MS (ESI): m/z=589.3 [M+H]$^+$.

Example 17. Synthesis of Compound I-21

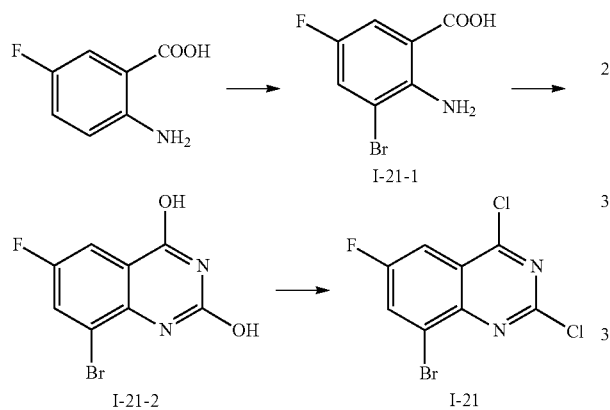

2-Amino-5-fluorobenzoic acid (10 g, 64.5 mmol) was dissolved in DMF (50 mL), and the mixture was added with NBS (12.6 g, 70.9 mmol) in portions while stirring at room temperature. After the addition was completed, the mixture was stirred at room temperature overnight. The reaction solution was added with water (120 mL) and a solid was precipitated. The mixture was filtered, and the filter cake was washed with water and dried to obtain compound I-21-1 (15 g, 100% yield) as a yellow solid. LC-MS (ESI): m/z=234.1 [M+H]+.

To a flask, compound I-21-1 (15 g, 64.1 mmol) and urea (38.5 g, 641 mmol) were added and the mixture was incubated 180° C. for 5 h. The reaction solution was cooled to about 100° C. and water was added for 2 h of resuspension. The mixture was filtered, and the filter cake was resuspended in water, filtered and dried twice to obtain compound I-21-2 (16 g, 96% yield) as a yellow solid. LC-MS (ESI): m/z=259.0 [M+H]$^+$.

Compound I-21-2 (16 g, 61.8 mmol) and phosphorus oxychloride (95 g, 618 mmol) were added to a flask before DIPEA (16 g, 123.6 mmol) was added dropwise at room temperature. After the addition was completed, the reaction solution was incubated at 110° C. for 2 h. The reaction solution was concentrated and the concentrate was slowly added to ice-water. The mixture was stirred for 10 min and filtered. The filter cake was dried to obtain compound I-21 (19 g, 100% yield).

Example 18. Synthesis of Compound II-21

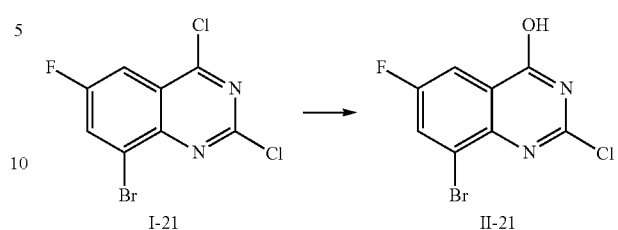

To a solution of compound I-21 (19 g, 64.2 mmol) in acetonitrile (240 mL), an aqueous sodium hydroxide solution (2 N, 128 mL) was added at room temperature. After the addition was completed, the reaction solution was stirred at 45° C. overnight, cooled to room temperature, and then, in an ice-water bath, slowly added with an aqueous hydrochloric acid solution (2 N) to adjust the pH to 5-6. A solid was precipitated. The mixture was filtered, and the filter cake was washed with water and dried to obtain compound II-21 (10.3 g, 58%). LC-MS (ESI): m/z=277.0 [M+H]$^+$.

Example 19. Synthesis of Compound II-21

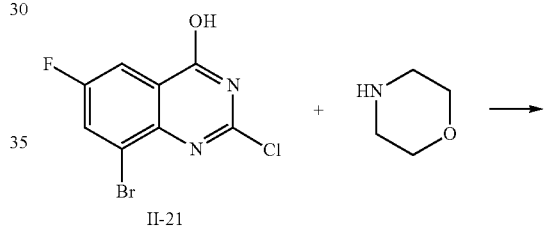

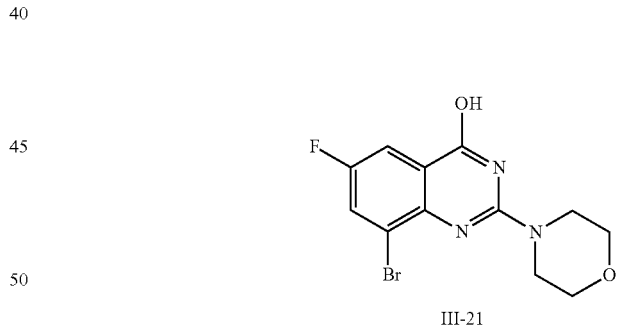

To a solution of compound II-21 (10.3 g, 37.1 mmol) in DMAC (60 mL), morpholine (8.1 g, 92.8 mmol) was added at room temperature. After the addition was completed, the reaction solution was stirred at 85° C. for 2 h. The reaction solution was cooled to room temperature, and then transferred to an ice-water bath before water (70 mL) was slowly added. A solid was precipitated. The mixture was filtered, and the filter cake was dried to obtain compound III-21 (8 g, 66% yield). LC-MS (ESI): m/z=328.1[M+H]$^+$.

Example 20. Synthesis of Compound IV-21

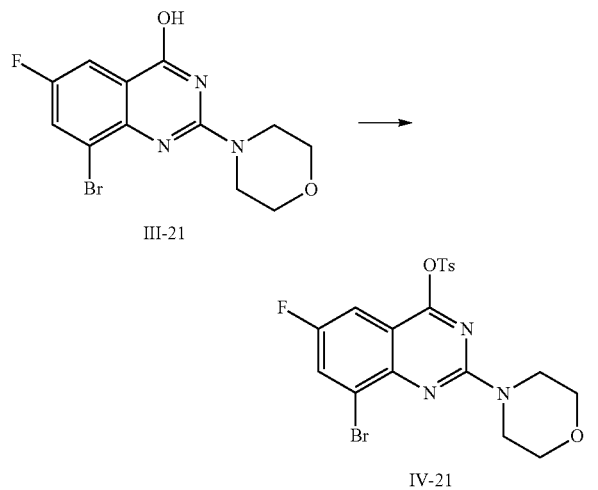

To a solution of compound III-21 (0.5 g, 1.52 mol) in acetonitrile (10 mL), potassium carbonate (274 mg, 1.98 mmol) and p-toluenesulfonyl chloride (290 mg, 1.52 mol) were added at room temperature. After the addition was completed, the reaction solution was stirred at 80° C. for 2 h. The reaction solution was cooled to room temperature, transferred to an ice-water bath, and dropwise added with water with the temperature controlled at 25° C. or less.

After the addition was completed, the mixture was continuously stirred for 1 h. The mixture was filtered, and the filter cake was washed with water and dried to obtain compound IV-21 (650 mg, 88% yield) as a yellow solid. LC-MS (ESI): m/z=482.1[M+H]t

Example 21. Synthesis of Compound V-21

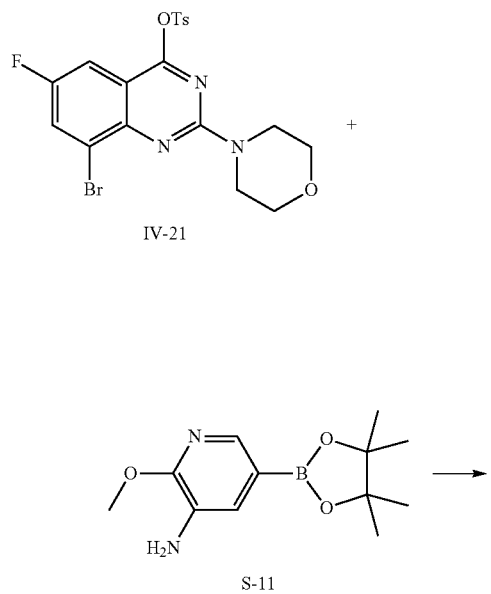

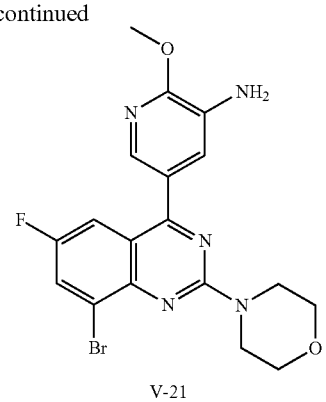

To a flask, the compounds IV-21 (200 mg, 0.41 mmol) and S-11 (104 mg, 0.41 mmol), tetrakis(triphenylphosphine) palladium (47 mg, 0.041 mmol), sodium carbonate (130 mg, 1.23 mmol), toluene (7.5 mL), isopropanol (2.5 mL) and water (3 mL) were added. The reaction solution was purged with nitrogen, and incubated 40° C. for 4 h. The reaction solution was concentrated by rotary evaporation, added with water, and extracted with ethyl acetate. The organic phase was washed with water, dried over anhydrous sodium sulfate and concentrated. The crude product was purified by column chromatography (PE:EA=3:1) to obtain compound V-21 (140 mg, 78% yield) as a yellow solid. LC-MS (ESI): m/z=434.1[M+H]$^+$.

Example 22. Synthesis of Compound VI-21

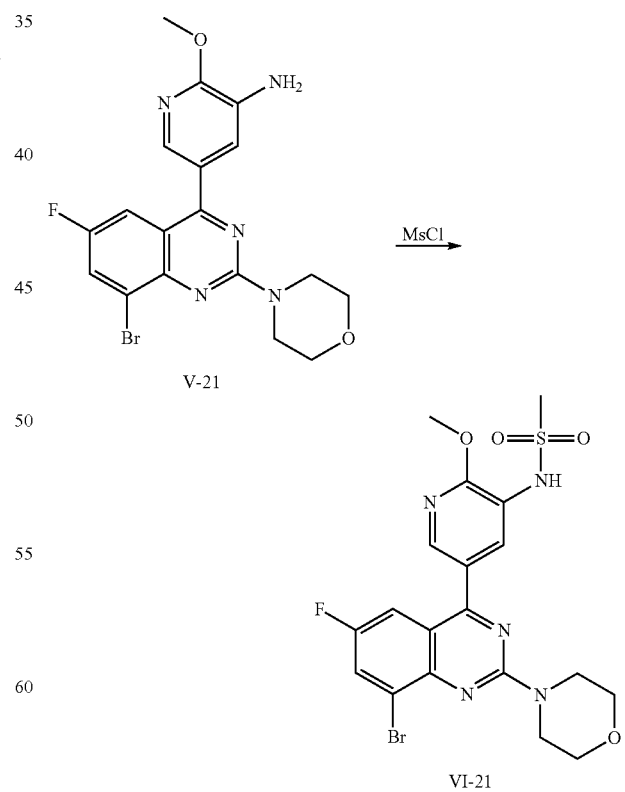

To a solution of compound V-21 (140 mg, 0.32 mmol) in pyridine (5 mL) in an ice bath, MSCl (37 mg, 0.32 mmol)

was added. The reaction solution was stirred at room temperature overnight, concentrated by rotary evaporation, added with water, and extracted with ethyl acetate. The organic phase was dried over anhydrous sodium sulfate and concentrated by rotary evaporation to obtain compound VI-21 (160 mg, 97% yield). LC-MS (ESI): m/z=512.1 [M+H]$^+$.

Example 23. Synthesis of Compound YY-20394

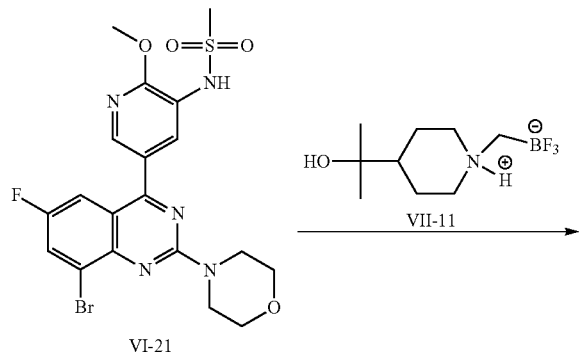

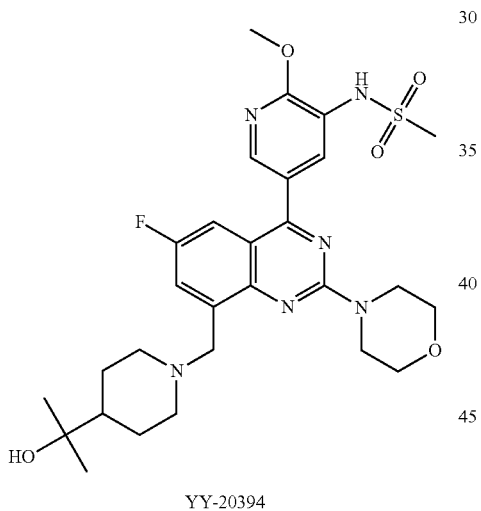

To a 10-mL microwave tube, the compounds VI-21 (140 mg, 0.27 mmol) and VII-11 (308 mg, 1.37 mmol), palladium acetate (6 mg, 0.027 mmol), x-Phos (26 mg, 0.054 mmol), cesium carbonate (264 mg, 0.81 mmol), THF (2 mL) and water (0.5 mL) were added. The microwave tube was purged with nitrogen. The reaction solution was incubated at 80° C. overnight. The reaction solution was concentrated by rotary evaporation, added with water, and extracted with ethyl acetate. The organic phase was washed with water, dried over anhydrous sodium sulfate and concentrated. The crude product was purified by preparative TLC (DCM:MeOH=30: 1) to obtain compound YY-20394 (80 mg, 50% yield) as a yellow solid. LC-MS (ESI): m/z =589.4[M+H]$^+$.

Example 24: Synthesis of Compound V-11

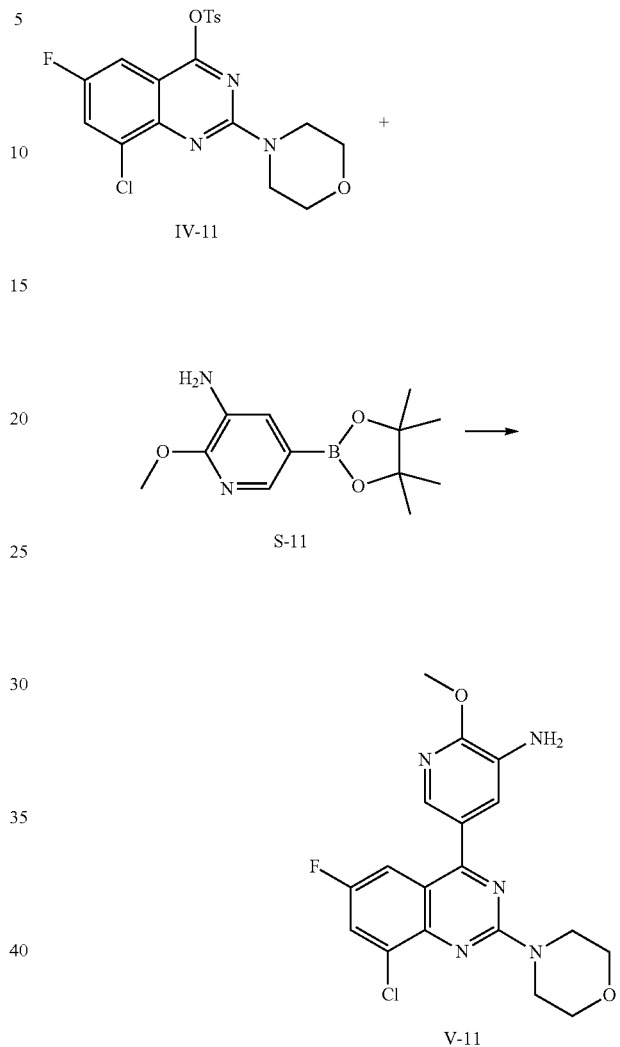

To a flask, the compounds IV-11 (159 mg, 0.36 mmol, 1 eq.) and S-11 (100 mg, 0.40 mmol, 1.1 eq.), sodium carbonate (385 mg, 3.63 mmol, 10 eq.), toluene (4.3 mL), isopropanol (1.5 mL) and water (2 mL) were added. The reaction solution was purged with nitrogen three times, and tetrakis(triphenylphosphine)palladium (21 mg, 0.018 mmol, 0.05 eq.) was added in nitrogen atmosphere. After the addition was completed, the reaction solution was stirred at 35-40° C. for 1 h and subjected to LC-MS. When compound IV-11 in the reaction solution was completely converted, the content of compound V-11 was 72.59% (wavelength 214 nm) and 99.03% (wavelength 254 nm). After the reaction was completed, the reaction solution was concentrated by rotary evaporation, added with water, and extracted with ethyl acetate (25 mL). The organic phase was concentrated by rotary evaporation, and purified by silica gel column chromatography (PE:EA=2:1) to obtain compound V-11 (142 mg, 92% yield) as a yellow solid with purities of 85.41% (wavelength 214 nm) and 91.71% (wavelength 254 nm) (the yield was calculated as per the purity 91.71% at wavelength 254 nm in LC-MS).

Comparative Example 1

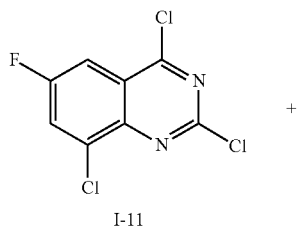

I-11

+

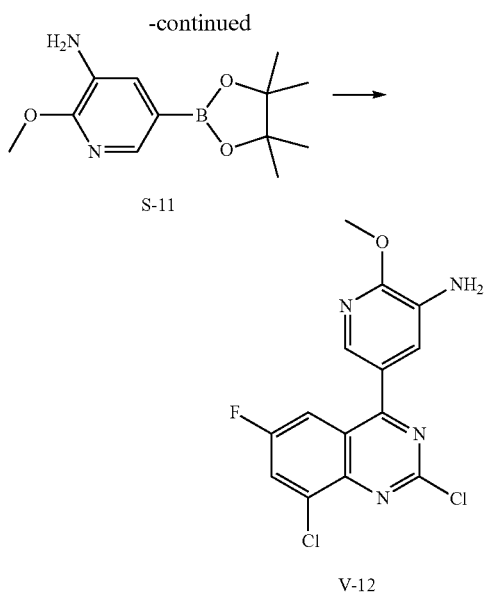

Compound IV-11 in Example 24 was replaced by compound I-11 (91 mg, 0.36 mmol, 1 eq.). According to the Suzuki reaction in the conditions of Example 24, the reaction solution was stirred at 35-40° C. for 1 h, and subjected to LC-MS. Through the assay, the content of compound V-12 was 28.64% (wavelength 214 nm) and 35.39% (wavelength 254 nm), with the presence of large amounts of reactants I-11 and S-11. The reaction solution was continuously stirred at 35-40° C. overnight, and subjected to LC-MS. Through the assay, some reactant I-11 and S-11 were still present in the reaction solution, and the content of compound V-12 was 35.28% (wavelength 214 nm) and 65.04% (wavelength 254 nm). After the reaction was completed, the reaction solution was concentrated by rotary evaporation, added with water, and extracted with ethyl acetate (25 mL). The organic phase was concentrated, and purified by column chromatography (PE:EA=4:1) to obtain compound V-12 (73 mg, 50% yield) as a yellow solid with purities of 84.62% (wavelength 214 nm) and 96.08% (wavelength 254 nm) (the yield was calculated as per the purity 96.08% at wavelength 254 nm in LC-MS).

This comparative example compared the Suzuki reaction using the compounds I-11 and IV-11 in the same conditions, and the results are summarized in Table 1.

TABLE 1

| | Content of product in reaction solution/% | | | | | Mass of purified product/mg | Yield of purified product/% |
|---|---|---|---|---|---|---|---|
| | 1 h | | Overnight | | | | |
| No. | Wavelength 214 nm | Wavelength 254 nm | Wavelength 214 nm | Wavelength 254 nm | Purity after purification/% | | |
| Example 24 | 72.59 | 99.03 | / | / | 85.4 (wavelength 214 nm), 91.71 (wavelength 254 nm) | 142 | 92 |
| Comparative example 1 | 28.64 | 35.39 | 35.28 | 65.04 | 84.6 (wavelength 214 nm), 96.08 (wavelength 254 nm) | 73 | 50 |

Note:
In Table 1, "/" indicates no detection.

From the results in Table 1, it is understood that the substituent at position 2 in the quinoline ring will affect the rate, progress, effect and yield of the Suzuki reaction in the same conditions. Compared with the substrate I-11 (namely the compound with chlorine at position 2 in the quinoline ring disclosed in Patent No. WO2015055071A1), the reaction time with the substrate IV-11 can be reduced to 1 hour, and the yield is improved by 42%, thus giving an elevated production efficiency and improved cost-efficiency, which cannot be expected on the basis of the prior art. The inventors of the present application, through continuous attempt and screening, have creatively found that when using the substrate IV-11, the Suzuki reaction may provide a higher yield in a reduced period of time, and side reactions at position 2 in the quinoline ring may also be avoided, which is advantageous for post-treatment.

Although specific embodiments of the present invention have been described above, it will be appreciated by those skilled in the art that these embodiments are merely illustrative and that many changes or modifications can be made to these embodiments without departing from the principles and spirit of the present invention. The scope of protection of the present invention is therefore defined by the appended claims.

What is claimed is:
1. A method for preparing a compound of formula V, comprising:
in the presence of a palladium catalyst and an alkaline reagent, performing a Suzuki reaction of compound S and compound IV as represented by the following formula in a solvent to obtain compound V;

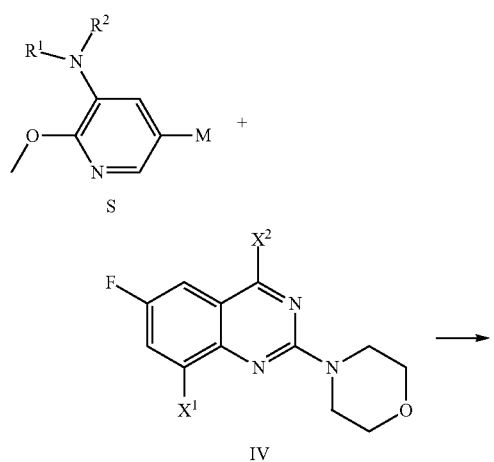

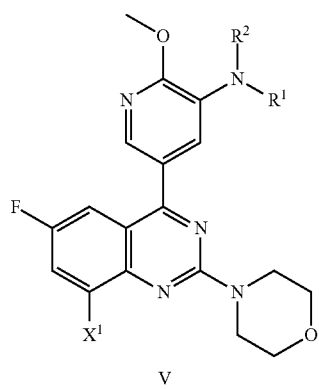

wherein R¹ and R² are independently H or

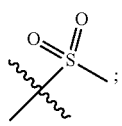

M is

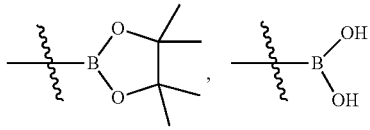

or —BF₃K;
X¹ is Cl or Br; X² is halogen,

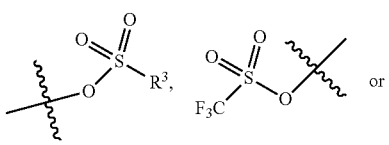

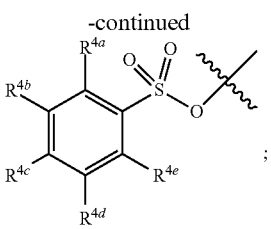

$R^3$ is $C_{1-4}$ alkyl; $R^{4a}$, $R^{4b}$, $R^{4c}$, $R^{4d}$ and $R^{4e}$ are independently H, $C_{1-6}$ alkyl, nitro or halogen.

2. The method according to claim 1, wherein in $X^2$, the halogen is Cl, Br or I;
and/or, in $R^3$, the $C_{1-4}$ alkyl is methyl, ethyl, n-propyl, isopropyl, n-butyl,

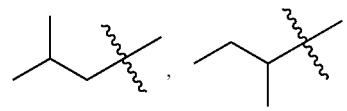

or tert-butyl;
and/or, in $R^{4a}$, $R^{4b}$, $R^{4c}$, $R^{4d}$ and $R^{4e}$, the halogen is independently Cl, Br or I;
and/or, in $R^{4a}$, $R^{4b}$, $R^{4c}$, $R^{4d}$ and $R^{4e}$, the $C_{1-6}$ alkyl is independently $C_{1-3}$ alkyl.

3. The method according to claim 1, wherein in $X^2$, the halogen is Cl;
and/or, in $R^3$, the $C_{1-4}$ alkyl is methyl;
and/or, in $R^{4a}$, $R^{4b}$, $R^{4c}$, $R^{4d}$ and $R^{4e}$, the $C_{1-6}$ alkyl is independently methyl, ethyl, n-propyl or isopropyl.

4. The method according to claim 1, wherein M is

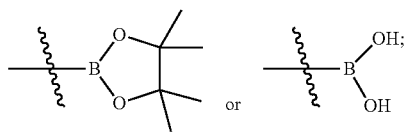

and/or, $X^1$ is Cl;
and/or, $X^2$ is halogen,

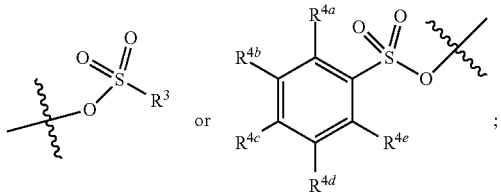

and/or, $R^{4a}$, $R^{4b}$, $R^{4d}$ and $R^{4e}$ are independently H.

5. The method according to claim 1, where M is

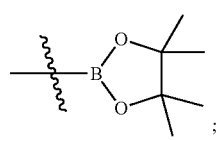 [SMILES: *B1OC(C)(C)C(C)(C)O1]

and/or, X² is

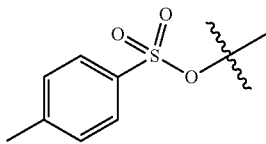

6. The method according to claim 1, wherein in the Suzuki reaction, the palladium catalyst is one or more of tetrakis(triphenylphosphine)palladium, palladium acetate, bis(triphenylphosphine)palladium dichloride, dichlorobis (tri-o-tolylphosphine)palladium(II), tris(dibenzylideneacetone)dipalladium, bis (tri-tert-butylphosphine)palladium (Pd[P(t-Bu)₃]₂), [1,1'-bis(diphenylphosphino)ferrocene]palladium dichloride, and [1,1'-bis(diphenylphosphino)ferrocene]palladium dichloride dichloromethane complex;

and/or, in the Suzuki reaction, the palladium catalyst reacts in the presence of a ligand; the ligand is one or more of triphenylphosphine, tris(o-tolyl)phosphine, tri-tert-butylphosphine tetrafluoroborate, 2-dicyclohexylphosphino-2',4',6'-triisopropylbiphenyl, 2-dicyclohexylphosphino-2',6'-dimethoxy-biphenyl and 2-dicyclohexylphosphino-2',6'-diisopropoxy-1,1'-biphenyl;

and/or, in the Suzuki reaction, the molar ratio of the palladium catalyst to compound IV is 0.01-0.5;

and/or, in the Suzuki reaction, the solvent is a mixed solvent of an organic solvent and water; the organic solvent is one or more of aromatic hydrocarbon solvent, alcohol solvent, chlorinated hydrocarbon solvent and ether solvent; the volume ratio of the organic solvent to the water is 1:1-10:1;

and/or, in the Suzuki reaction, the alkaline reagent is one or more of alkali metal carbonate, alkali metal fluoride, alkali metal phosphate, alkali metal tert-butoxide and alkali metal hydroxide;

and/or, in the Suzuki reaction, the molar ratio of the alkaline reagent to compound IV is 1-10;

and/or, in the Suzuki reaction, the molar ratio of compound S to compound IV is 0.9-3;

and/or, in the Suzuki reaction, the temperature of the Suzuki reaction is 0-130° C.;

and/or, the Suzuki reaction is performed in a protective gas atmosphere;

and/or, in the Suzuki reaction, compound S is

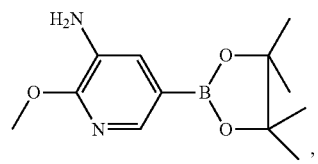
S-11

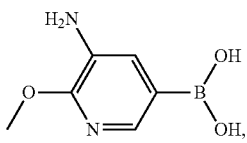
S-21

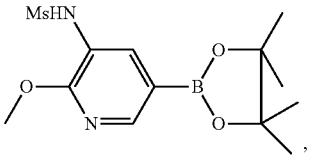
T-11

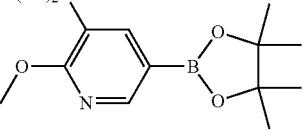
T-12

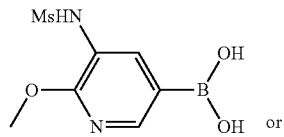
T-21

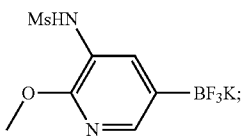
T-31 and/or, in the Suzuki reaction, compound IV is

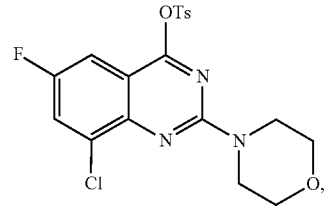
IV-11

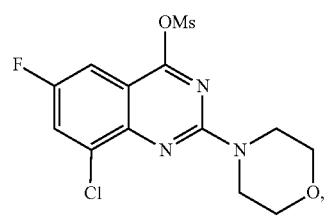
IV-12

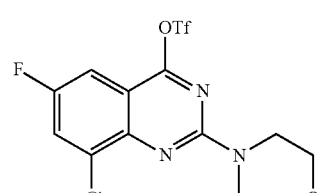
IV-13

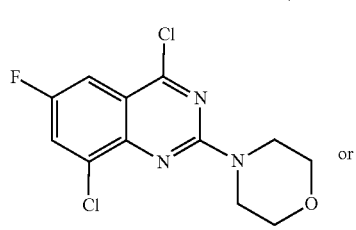
IV-14

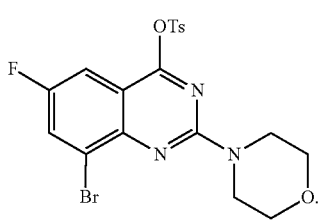

IV-21

7. The method according to claim 1, wherein in the Suzuki reaction, the palladium catalyst is tetrakis(triphenylphosphine)palladium;
    and/or, in the Suzuki reaction, the molar ratio of the palladium catalyst to compound IV is 0.02-0.2;
    and/or, in the Suzuki reaction, the solvent is a mixed solvent of aromatic hydrocarbon solvent and water solvent; the organic solvent is a mixed solvent of aromatic hydrocarbon solvent and alcohol solvent;
    and/or, the solvent is a mixed solvent of aromatic hydrocarbon solvent and water solvent; the volume ratio of the organic solvent to the water is 5:1-10:1;
    and/or, in the Suzuki reaction, the molar ratio of the alkaline reagent to compound IV is 2-10;
    and/or, in the Suzuki reaction, the molar ratio of compound S to compound IV is 0.9-1.5;
    and/or, in the Suzuki reaction, the temperature of the Suzuki reaction is 20-70° C.

8. The method according to claim 1, further comprising a method for preparing compound IV, wherein the method is method 1 or method 2:
    method 1 comprising: performing a halogenation reaction of compound III and phosphorus oxyhalide and/or phosphorus halide as represented by the following formula to obtain compound IV;
    method 2 comprising: in the presence of an alkaline reagent, performing a nucleophilic substitution reaction of compound III and a sulfonation reagent as represented by the following formula in an organic solvent to obtain compound IV;
    the sulfonation reagent is

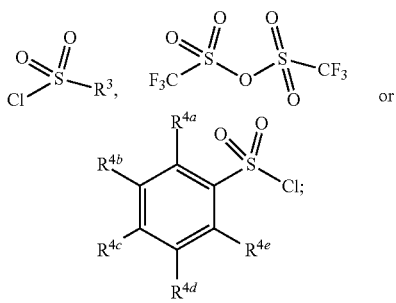

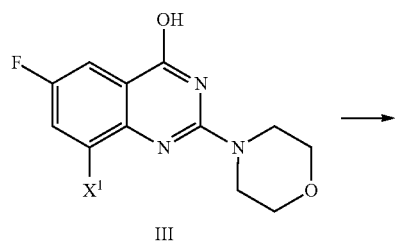

III

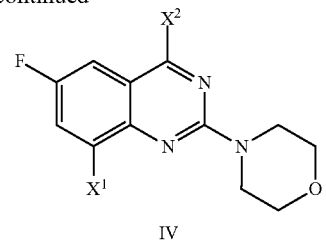

IV when $X^2$ is halogen, then the method for preparing compound IV is method 1;
when $X^2$ is

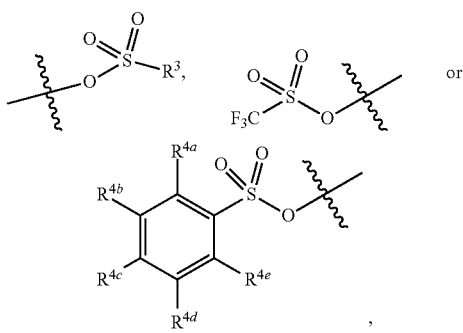

then the method for preparing compound IV is method 2.

9. The method according to claim 8, wherein in method 1, the halogenation reaction is a neat reaction;
    and/or, in method 1, the halogen in the phosphorus oxyhalide and/or phosphorus halide is Cl, Br or I;
    and/or, in method 1, the molar ratio of the phosphorus oxyhalide and/or phosphorus halide to compound III is greater than or equal to 1;
    and/or, in method 1, the temperature of the halogenation reaction is 20-130° C.;
    and/or, in method 2, the alkaline reagent is a weak organic alkali and/or a weak inorganic alkali salt;
    and/or, in method 2, when the sulfonation reagent is

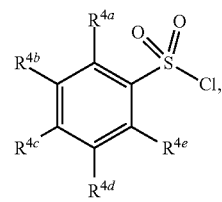

the

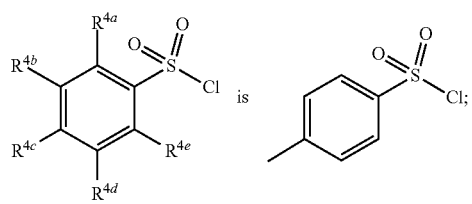

and/or, in method 2, when the sulfonation reagent is

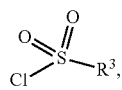

the

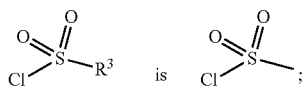

and/or, in method 2, the molar ratio of the sulfonation reagent to compound III is 1-1.5;

and/or, in method 2, the organic solvent is one or more of a nitrile solvent, a chlorinated hydrocarbon solvent and an ether solvent;

and/or, in method 2, the volume-to-mass ratio of the organic solvent to compound III is 5-15 mL/g.

10. The method according to claim 8, wherein in method 1, the halogen in the phosphorus oxyhalide and/or phosphorus halide is Cl;

and/or, in method 1, the molar ratio of the phosphorus oxyhalide and/or phosphorus halide to compound III is 1-30;

and/or, in method 1, the temperature of the halogenation reaction is 60-110° C.;

and/or, in method 2, the alkaline reagent is a weak organic alkali and/or a weak inorganic alkali salt, and the organic weak alkali is a tertiary amine weak organic alkali and/or a pyridine weak organic alkali; the weak inorganic alkaline salt is an alkali metal carbonate.

11. The method according to claim 8, further comprising:

performing a nucleophilic substitution reaction of compound II and compound A as represented by the following formula in an organic solvent to obtain compound III;

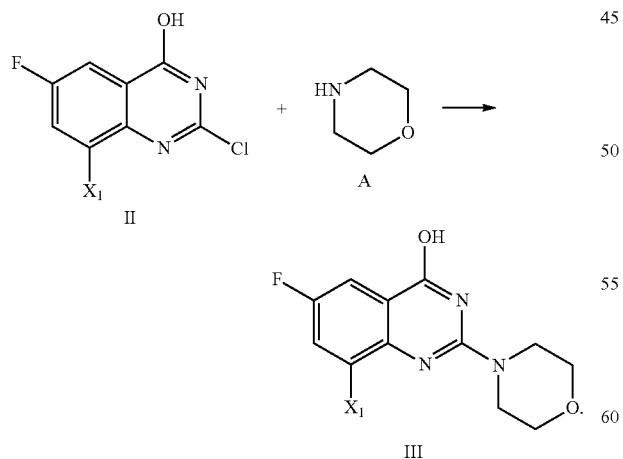

12. The method according to claim 11, further comprising: in the presence of an alkaline reagent, performing a reaction of compound I as represented by the following formula to obtain compound II;

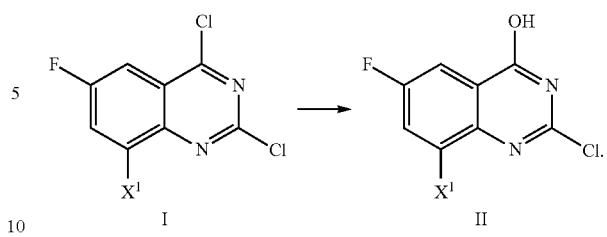

13. A method for preparing a compound of formula YY-20394, comprising:

step S1: in the presence of a palladium catalyst and an alkaline reagent, performing a Suzuki reaction of compound S and compound IV as represented by the following formula in a solvent to obtain compound V;

step S2: in the presence of an alkaline reagent, performing a reaction of methylsulfonyl chloride and compound V as represented by the following formula in an organic solvent to obtain compound VI;

step S3: in the presence of an alkaline reagent and in the presence of a palladium catalyst and a ligand, performing a conjugation reaction of compound VII and compound VI as represented by the following formula in a solvent to obtain compound YY-20394;

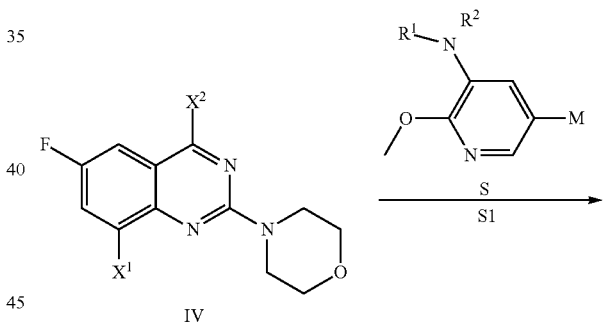

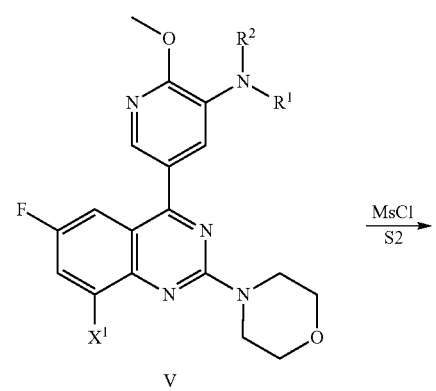

-continued

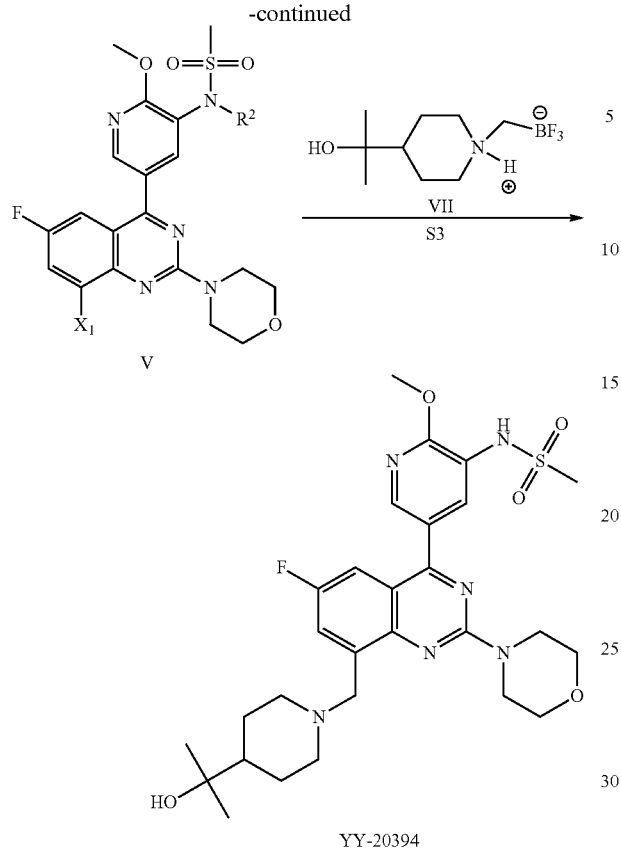

V

YY-20394 wherein, when $R^1$ and $R^2$ in compound V are both

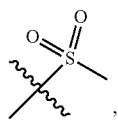 [SMILES: *S(C)(=O)=O]

compound V is directly subjected to the conjugation reaction in step S3 without step S2;
in step S1, the conditions and procedures of the method for preparing compound V are as defined in claim 1.

14. The method according to claim 13, wherein in the method for preparing the compound of formula YY-20394, when $R^1$ and $R^2$ in compound V are not both H or

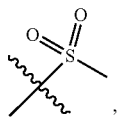 [SMILES: *S(C)(=O)=O]

compound V is directly subjected to the conjugation reaction in step S3 without step S2;
and/or, in step S2, the alkaline reagent is a weak organic alkali;
and/or, in step S2, the molar ratio of methylsulfonyl chloride to compound V is 1-5;
and/or, in step S2, the molar ratio of the alkaline reagent to compound V is 3-25;
and/or, in step S2, the organic solvent is a chlorinated hydrocarbon solvent;
and/or, in step S2, the reaction temperature is 10-50° C.;
and/or, in step S2, compound V is

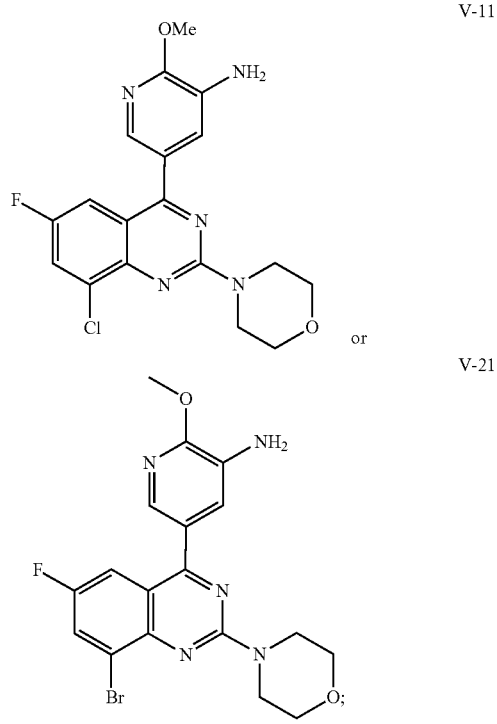

and/or, in step S3, the palladium catalyst is one or more of tetrakis(triphenylphosphine)palladium, palladium acetate, bis(triphenylphosphine)palladium dichloride, dichlorobis(tri-o-tolylphosphine)palladium(II), tris (dibenzylideneacetone) dipalladium, bis(tri-tert-butylphosphine)palladium $(Pd[P(t-Bu)_3]_2)$, [1,1'-bis (diphenylphosphino) ferrocene]palladium dichloride, and [1,1'-bis(diphenylphosphino)ferrocene]palladium (II) dichloride dichloromethane complex;
and/or, in step S3, the molar ratio of the palladium catalyst to compound VI is 0.01-0.2;
and/or, in step S3, the ligand is one or more of triphenylphosphine, tris (o-tolyl)phosphine, tri-tert-butylphosphine tetrafluoroborate, 2-dicyclohexylphosphino-2', 4',6'-triisopropylbiphenyl, 2-dicyclohexylphosphino-2',6'-dimethoxy-biphenyl and 2-dicyclohexylphosphino-2',6'-diisopropoxy -1,1'-biphenyl;
and/or, in step S3, the molar ratio of the ligand to compound VI is 0.02-0.4;
and/or, in step S3, the alkaline reagent is one or more of alkali metal carbonate, alkali metal fluoride, alkali metal phosphate, alkali metal tert-butoxide and alkali metal hydroxide;
and/or, in step S3, the molar ratio of the alkaline reagent to compound VI is 1-20;
and/or, in step S3, the molar ratio of compound VII to compound VI is 0.8-6;
and/or, in step S3, the solvent is a mixed solvent of a water-soluble organic solvent and water; the organic solvent is a water-soluble organic solvent; the volume ratio of the water-soluble organic solvent to water is 1:1-15:1;

and/or, in step S3, compound VI is

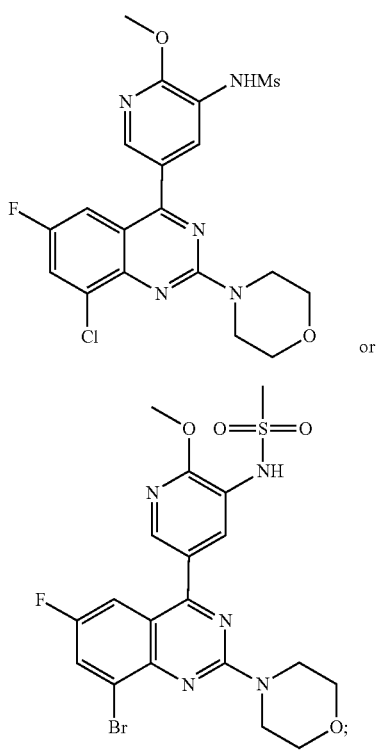

and/or, in step S3, the conjugation reaction is performed in a protective gas atmosphere, wherein the protective gas is nitrogen or argon.

15. The method according to claim 13, wherein
in step S2, the alkaline reagent is a weak organic alkali; the weak organic alkali is a pyridine weak organic alkali and/or a tertiary amine weak organic alkali;
and/or, in step S2, the organic solvent is dichloromethane;
and/or, in step S3, the palladium catalyst is palladium acetate;
and/or, in step S3, the ligand is 2-dicyclohexylphosphino-2',4',6'-triisopropylbiphenyl;
and/or, in step S3, the molar ratio of compound VII to compound VI is 1-3;
and/or, in step S3, the solvent is a mixed solvent of a water-soluble organic solvent and water; the organic solvent is a water-soluble organic solvent; the water-soluble organic solvent is an ether solvent and/or an alcohol solvent;
and/or, in step S3, the solvent is a mixed solvent of a water-soluble organic solvent and water; the organic solvent is a water-soluble organic solvent; the volume ratio of the water-soluble organic solvent to water is 3:1-15:1.

16. The method according to claim 13, wherein
in step S2, the alkaline reagent is a weak organic alkali; the weak organic alkali is a pyridine weak organic alkali;
and/or, in step S3, the solvent is a mixed solvent of a water-soluble organic solvent and water; the organic solvent is a water-soluble organic solvent; the water-soluble organic solvent is an ether solvent.

17. The method according to claim 13, wherein
in step S2, the alkaline reagent is a weak organic alkali; the weak organic alkali is pyridine;
and/or, in step S3, the solvent is a mixed solvent of a water-soluble organic solvent and water; the organic solvent is a water-soluble organic solvent; the water-soluble organic solvent is one or more of tetrahydrofuran, 1,4-dioxane and ethylene glycol dimethyl ether.

18. The method according to claim 13, wherein in step S3, the solvent is a mixed solvent of a water-soluble organic solvent and water; the organic solvent is a water-soluble organic solvent; the water-soluble organic solvent is tetrahydrofuran.

19. A compound of formula IV:

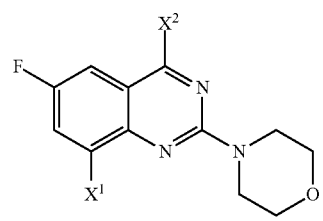

wherein $X^1$ and $X^2$ are as defined in claim 1;
or, a compound of formula III:

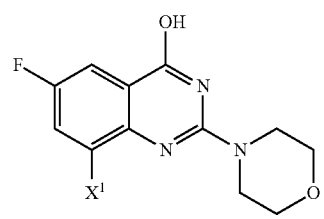

wherein $X^1$ is Cl or Br;
or, a compound of formula II:

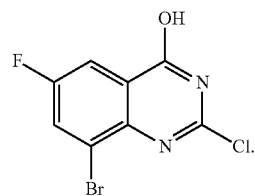 [SMILES: Oc1nc(Cl)nc2c(Br)cc(F)cc12]

20. Compound IV according to claim 19, wherein compound IV is

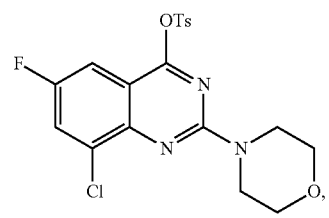

IV-12
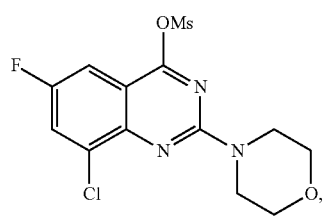
IV-13
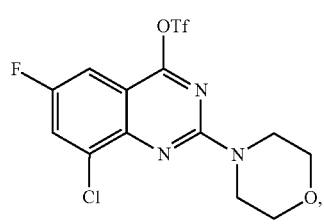
IV-14
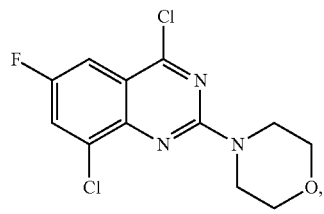
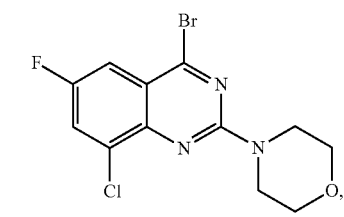
IV-21
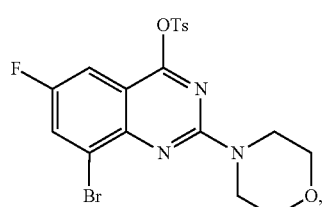
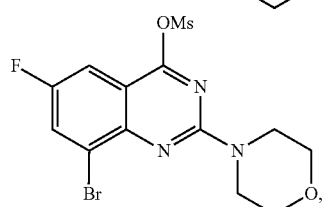
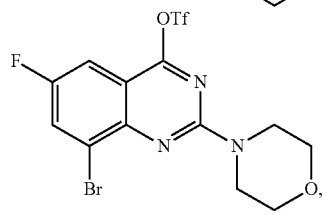
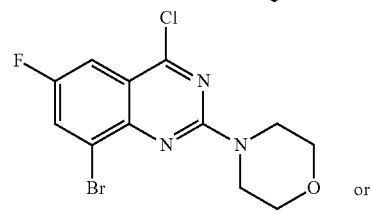 or
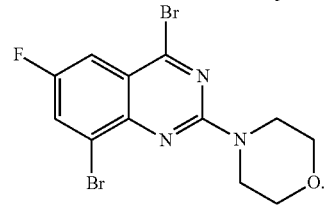.
* * * * *